(12) United States Patent
Boyd et al.

(10) Patent No.: US 6,824,305 B1
(45) Date of Patent: Nov. 30, 2004

(54) LOCAL WALL HEAT FLUX/TEMPERATURE METER FOR CONVECTIVE FLOW AND METHOD OF UTILIZING SAME

(75) Inventors: Ronald D. Boyd, Spring, TX (US); Ali Ekhlassi, Tomball, TX (US); Penrose Cofie, Houston, TX (US)

(73) Assignee: The Texas A & M University System, College Station, TX (US)

( * ) Notice: Subject to any disclaimer, the term of this patent is extended or adjusted under 35 U.S.C. 154(b) by 0 days.

(21) Appl. No.: 10/641,826

(22) Filed: Aug. 15, 2003

Related U.S. Application Data

(60) Provisional application No. 60/404,246, filed on Aug. 16, 2002.

(51) Int. Cl.$^7$ .............................. G01K 17/00; G01K 3/06
(52) U.S. Cl. .............................. 374/29; 374/30; 374/44; 374/15
(58) Field of Search ........................... 374/29, 30, 44, 374/137, 134, 110, 112, 15, 135, 45

(56) References Cited

U.S. PATENT DOCUMENTS

| | | | | |
|---|---|---|---|---|
| 3,263,485 A | * | 8/1966 | Mahmoodi .................... | 374/44 |
| 6,331,075 B1 | * | 12/2001 | Amer et al. ................... | 374/44 |
| 6,487,866 B1 | * | 12/2002 | Fesmire et al. ............... | 62/51.1 |
| 6,497,509 B2 | * | 12/2002 | Merzliakov et al. .......... | 374/44 |
| 6,742,926 B1 | * | 6/2004 | Fesmire et al. ............... | 374/45 |
| 2003/0196778 A1 | * | 10/2003 | Kobayashi et al. ........... | 165/41 |

OTHER PUBLICATIONS

Boyd, et al., "Similarities and Differences Between Single-–Side and Uniform Heating for Fusion Applications–I: Uniform Heat Flux," Fusion Technology, vol. 25, 1994, pp. 411–418, Jul., 1994.

Problems #1 & #2 from Final Exam of MCEG 5153 (1 page), Thermal Science Research Center, College of Engineering, A&M University, Prairie View, TX, Fall, 1996.

Boyd, Sr., et al., "Single–Side Heated Monoblock, High Heat Flux Removal Using Water Subcooled Turbulent Flow Boiling", Journal of Heat Transfer, ASME, Thermal Science Research Center, College of Engineering, A&M University, Prairie View, TX, Feb. 2004, vol. 126 (5 pages).

Boyd, Sr. et al., "Conjugate Heat Transfer Measurements In A Single–Side Heated Circular Flow Channel Under Turbulent, Subcooled Flow Boiling Conditions", presented at the Twelfth International Heat Transfer Conference, Gremble, France, Aug. 18–23, 2002 (6 pages).

* cited by examiner

*Primary Examiner*—Gail Verbitsky
(74) *Attorney, Agent, or Firm*—Baker Botts L.L.P.

(57) ABSTRACT

According to one embodiment of the invention, a method includes providing a conduit having a fluid flowing therethrough, disposing a plurality of temperature measurement devices inside a wall of the conduit, positioning at least some of the temperature measurement devices proximate an inside surface of the wall of the conduit, positioning at least some of the temperature measurement devices at different radial positions at the same circumferential location within the wall, measuring a plurality of temperatures of the wall with respective ones of the temperature measurement devices to obtain a three-dimensional temperature topology of the wall, determining the temperature dependent thermal conductivity of the conduit, and determining a multi-dimensional thermal characteristic of the inside surface of the wall of the conduit based on extrapolation of the three-dimensional temperature topology and the temperature dependent thermal conductivities.

36 Claims, 15 Drawing Sheets

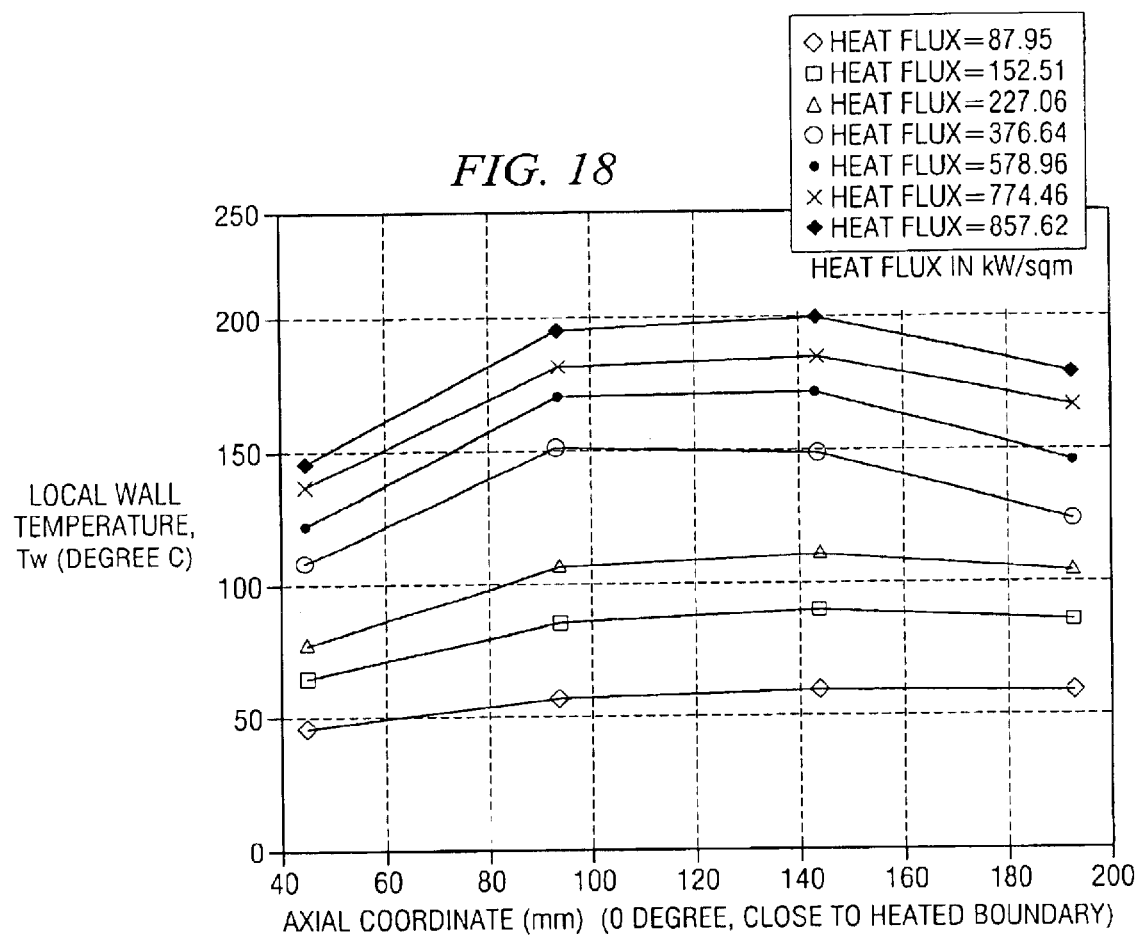

LOCAL WALL HEAT FLUX/TEMPERATURE METER FOR CONVECTIVE FLOW AND METHOD OF UTILIZING SAME

RELATED APPLICATIONS

This application claims the benefit of Ser. No. 60/404,246, titled "LOCAL WALL HEAT FLUX/TEMPERATURE METER FOR CONVECTIVE FLOW AND METHOD OF UTILIZING SAME," filed provisionally on Aug. 16, 2002.

GOVERNMENT RIGHTS

This invention was made with Government support from the Department of Energy (DOE Grant #DE-FG03-97ER-54452) and the National Aeronautics and Space Administration (NASA Contract NAG 9-310). The government may have certain rights in this invention.

TECHNICAL FIELD OF THE INVENTION

The present invention relates generally to the fluid flow meters and, more particularly, to a local wall heat flux/temperature meter for convective fluid flow and method for utilizing the same.

BACKGROUND OF THE INVENTION

Since the design requirements, goals, and objectives of plasma-facing components (PFCs) and electronic heat sinks (EHSs) are evolving, the development of an experimental conjugate multi-dimensional, flow boiling database may provide the basis for computational fluid dynamic (CFD) comparisons, flow boiling correlation modifications, and adaptations that include single-side heating effects for detail PFC and EHS flow channel and substrate design studies, which may lead to cost-effective and robust designs. Many papers have been published reporting either new or modified flow boiling correlations. Generally, there appears to be good confidence in predicting water flow boiling for uniformly heated circular channels with or without twisted tapes. However, most all PFCs and EHSs involve single-side heated flow channels and, hence, depend on at least two-dimensional, and in some cases three-dimensional, conjugate data and analysis for new or modified flow boiling or single-phase correlations with two- and possibly three-dimensional influences.

Conjugate heat transfer modeling has proven useful in forming baselines and identifying important parameters affecting peaking factors and data reduction for the spectrum of high heat fluxes found in a wide variety of applications. For various applications requiring different fluids, the results show the following: (1) the coexistence of three flow boiling regimes inside the single-side heated flow channel, (2) the correlational dependence of the inside wall heat flux and temperature (fluid independent), and (3) inaccuracies that could arise in some data reduction procedures (fluid independent). However, for PFC applications in fusion reactors, work to expand conjugate heat transfer analyses from simple circular and complex geometries to PFC geometries is still needed for consistently predicting peaking factors and prototypic conditions.

SUMMARY OF THE INVENTION

According to one embodiment of the invention, a method includes providing a conduit having a fluid flowing therethrough, disposing a plurality of temperature measurement devices inside a wall of the conduit, positioning at least some of the temperature measurement devices proximate an inside surface of the wall of the conduit, positioning at least some of the temperature measurement devices at different radial positions at the same circumferential location within the wall, measuring a plurality of temperatures of the wall with respective ones of the temperature measurement devices to obtain a three-dimensional temperature topology of the wall, determining the temperature dependent thermal conductivity of the conduit, and determining a multi-dimensional thermal characteristic of the inside surface of the wall of the conduit based on extrapolation of the three-dimensional temperature topology and the temperature dependent thermal conductivity.

Embodiments of the invention provide a number of technical advantages. Embodiments of the invention may include all, some, or none of these advantages. In one embodiment, a local wall heat flux/temperature meter allows measurement of 2-D wall-fluid interface thermal phenomena (heat flux, temperature and heat transfer coefficient) never before measured independent of fluid. The meter may assist in developing new and improved designs, may be independent of fluid flowing in channel, may assist in assessing sophisticated software (Computational Fluid Dynamic, CFD) used to numerically predict turbulent and multiphase fluid flows, and may be used in many industries (nuclear reactor and power generation, electronic cooling, medical, aircraft, spacecraft, chemical, petroleum, material processing, HVAC, non-destructive testing, CFD-user Industries, Automobile, safety, etc.), to monitor safety concerns that are directly related to the inside wall heat flux or temperature.

Other technical advantages are readily apparent to one skilled in the art from the following figures, descriptions, and claims.

BRIEF DESCRIPTION OF THE DRAWINGS

For a more complete understanding of the invention, and for further features and advantages, reference is now made to the following description, taken in conjunction with the accompanying drawings, in which:

FIGS. 12A, 12B and 12C are cross-sectional views of another conduit used for local temperature and/or heat transfer measurements illustrating example thermocouple locations according to one embodiment of the present invention;

FIG. 18 illustrates axial wall temperature profiles from the TCs at $\phi=0.0$ degrees, and close to the heated boundary as a function of the net incident heat flux ($L_o=4.0$ mm, and $L_i=16.0$ mm) according to one embodiment of the present invention.

DETAILED DESCRIPTION OF EXAMPLE EMBODIMENTS OF THE INVENTION

Example embodiments of the present invention and their advantages are best understood by referring now to FIGS. 1A through 18 of the drawings.

Figure 1A:
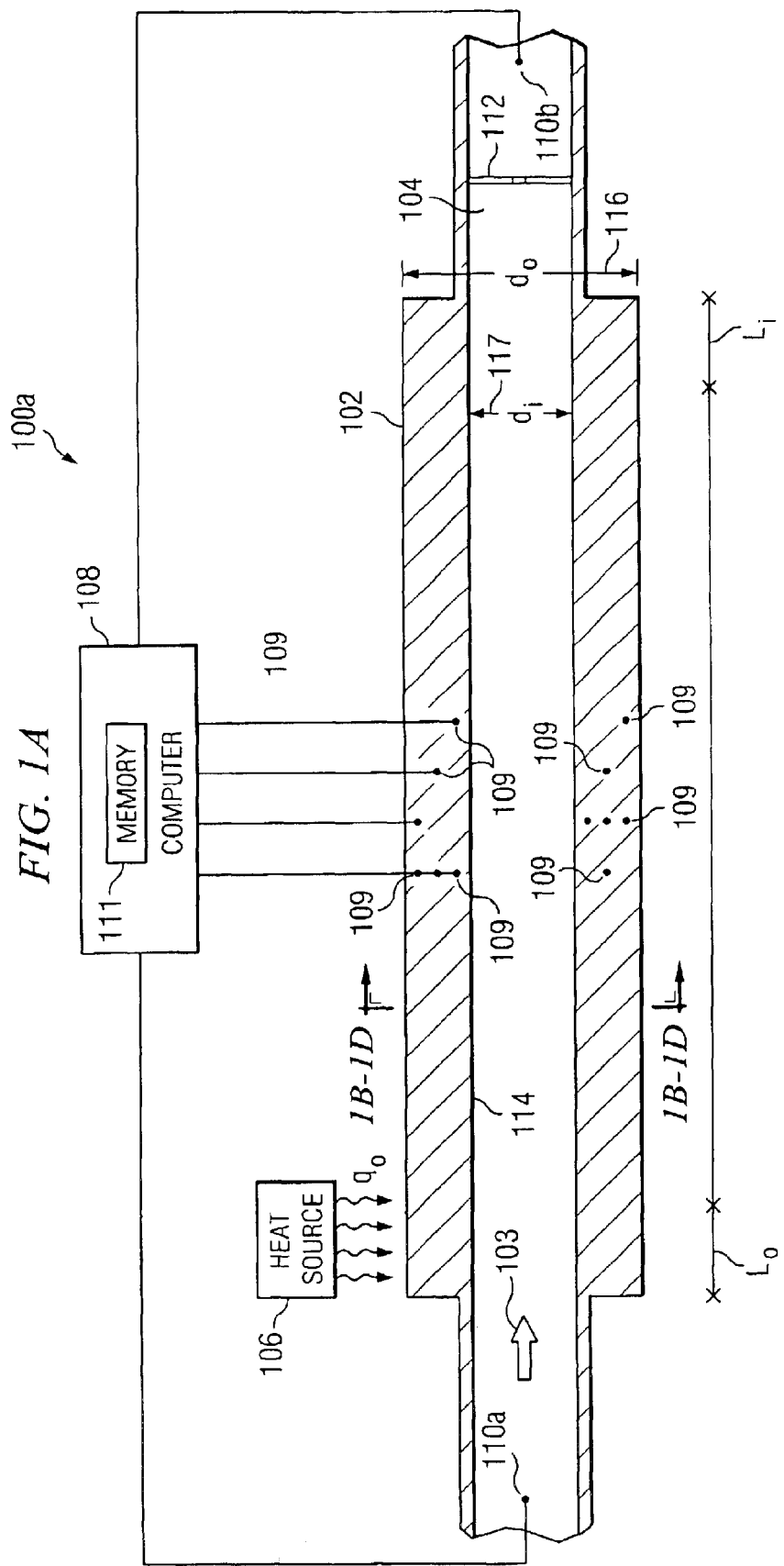
FIG. 1A is an elevation view of a conduit used for local temperature and/or heat transfer measurements according to one embodiment of the present invention.

Referring to FIG. 1A, a system 100a includes a conduit 102 having a fluid 103 flowing through a flow channel 104. Conduit 102 is being heated by a heat source 106, which may uniformly or non-uniformly heat the conduit 102. System 100a also includes a computer 108 having a memory 111 coupled to a plurality of temperature measuring devices 109 that are disposed within the wall of conduit 102, a pair of fluid thermocouples 110a, 110b that are disposed within fluid 103 at the inlet and outlet, respectively, and a flow measuring device 112. Although illustrated in FIG. 1A as having a generally cylindrical cross-section, conduit 102 may have any suitable configuration, depending on the particular application that conduit 102 is being used for. In addition, conduit 102 may be formed from any suitable material, such as a metal, a ceramic, a polymer, a composite material, or other suitable material.

As illustrated and described below in conjunction with FIGS. 1A through 11, system 100a is utilized within the teachings of one example embodiment of the invention to obtain two-dimensional distributions of wall temperature, heat flux and heat transfer coefficient of an inside surface 114 of flow channel 104 and the two-dimensional temperature gradient of fluid 103. As illustrated and described below in conjunction with FIGS. 12A through 18, a system 100b is utilized within the teachings of another example embodiment of the invention to obtain two-dimensional distributions of wall temperature, heat flux and heat transfer coefficient of an inside surface 114 of flow channel 104 and the two-dimensional temperature gradient of fluid 103. Some results of these example embodiments are presented below with water as fluid 103 for flow conditions ranging from single-phase to fully-developed subcooled flow boiling. However, the present invention contemplates other suitable fluids for fluid 103. Boiling curves, dimensionless representations, and tabulated reduced data are presented below.

Figure 1B:
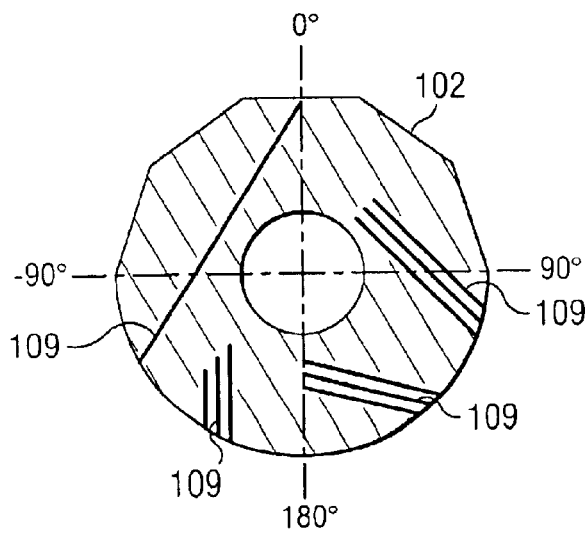
FIGS. 1B, 1C and 1D are cross-sectional views of the conduit of FIG. 1A illustrating example thermocouple locations according to one embodiment of the present invention.
Figure 1C:
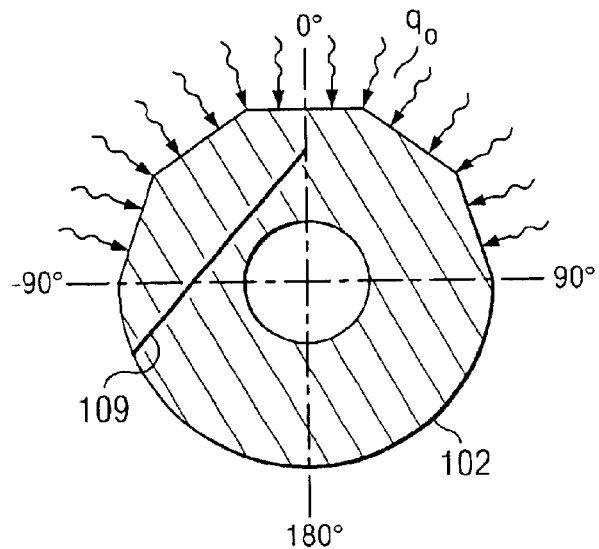

Referring to FIGS. 1A through 1D, the theoretical or idealization of a cylindrical-like test section is a circular cylinder with approximately half (−90 degrees to +90 degrees) of its outside boundary subjected to a uniform heat flux, $q_o$, (as illustrated in FIG. 1C for clarity purposes) and the remaining half insulated. In the illustrated example embodiment, an outside diameter 116 of conduit 102 is 30.0 mm, an inside diameter 117 is 10.0 mm, and its length is 200.0 mm; however, any suitable diameter and length for conduit 102 is contemplated by the invention. The actual directly heated length is approximately 180.0 mm. The lengths $L_i$ and $L_o$ shown in FIG. 1A are variable lengths whose sum should equal about 20.0 mm for a given experimental setup. The inlet water temperature may be set at any level in the range from 23.0° C. to 130.0° C. and the exit pressure may be set at any level in the range from 0.05 MPa to 4.0 MPa. The mass velocity may be set at any level in the range from 0.3 to 10.0 Mg/m²s.

Figure 1D:
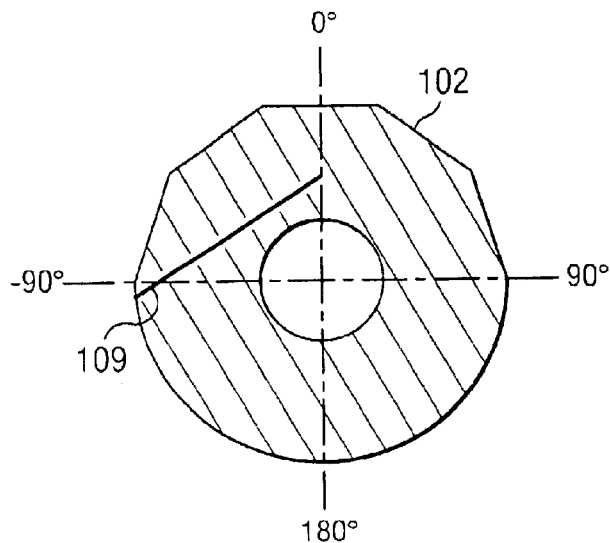

Temperature measuring devices 109, which in the illustrated embodiment are thermocouples but may be other suitable temperature measuring devices such as thermistors, are positioned within the wall of conduit 102 using any suitable method for local in-depth wall temperature measurements. In the example embodiment, thermocouples 109 are placed at forty-eight locations with each of four axial stations having three thermocouples 109 embedded at four different circumferential locations (0, 45, 180, and −135 degrees, where 0 degrees corresponds to that portion of the plane of symmetry close to heat flux $q_o$) in the wall of conduit 102. These locations of thermocouples 109 are illustrated in FIGS. 1B through 1D, which illustrate one of the four axial locations for thermocouples 109. A purpose of the four axial locations is to obtain an estimate of the axial distribution of the conduits wall temperature for a given applied heat flux, $q_o$. Although the positioning of thermocouples 109 is variable depending on the geometry of conduit 102 as well as other factors, it is important that at least some of thermocouples 109 are positioned proximate inside surface 114 of flow channel 104 and that at least some are positioned at different radial locations at the same circumferential location (see FIG. 1B for example).

Since the positioning of thermocouples 109 is similar at all four primary axial stations, a description is given for only one axial station. For example, the axial station in FIGS. 1B through 1D has twelve thermocouples 109, ten of which are shown in FIG. 1B, one of which is shown in FIG. 1C, and another of which is shown in FIG. 1D. FIGS. 1C and 1D illustrate planes that are axially displaced upstream from the plane of FIG. 1B by 2.0 mm and 4.0 mm, respectively. Thermocouples 109 will give both radial and circumferential distributions of the local wall temperature. Hence, a combination of all axial stations produces a three-dimensional distribution (topology) of conduit 102 local wall temperature as a function of the applied heat flux, $q_o$, and the water flow regime that may vary from single-phase at the inlet to subcooled flow boiling at the outlet.

In one embodiment of the invention, a method for determining a multi-dimensional thermal characteristic, such as the two-dimensional temperature or heat flux, of inside surface 114 of conduit 102 is as follows. This method may be performed by computer 108, manual calculations, or other suitable technique. First, fluid 103 flowing through conduit 102 is provided. Thermocouples 109 are disposed inside the wall of conduit 102, such that at least some of thermocouples 109 are proximate inside surface 114 of conduit 102 and at least some of thermocouples 109 are at different radial positions at the same circumferential location within the wall (see FIG. 1B for example). A plurality of temperatures of the wall of conduit 102 are measured with respective ones of thermocouples 109 to obtain a three-dimensional temperature topology of the wall. The temperature dependent thermal conductivity of conduit 102 is determined from suitable thermal conductivity tables, which may be stored in memory 111 of computer 108. And the multi-dimensional thermal characteristic of inside surface 114 of the wall of conduit 102 is determined based on extrapolation of the three-dimensional temperature topology and the temperature dependent thermal conductivity of conduit 102. In lieu of extrapolation, an inverse conduction computer code, utilizing computer 108, may be utilized to determine the multi-dimensional thermal characteristic.

The two-dimensional heat transfer coefficient or the two-dimensional temperature gradient of fluid 103 may also be determined. However, in this case, one would need the bulk inlet and outlet temperature of fluid 103, which may be measured using fluid thermocouples 110a, 110b, the mass flow rate of fluid 103, which may be measured using flow measurement device 112, as well as the temperature dependent thermal conductivity of fluid 102, which may be determined from suitable thermal conductivity tables. These values would be utilized to obtain the bulk fluid temperature variation along conduit 102 as well as the temperature dependent specific enthalpy variation of fluid 103, which may then be used to determine the two-dimensional heat transfer coefficient or the two-dimensional temperature gradient of fluid 103.

Figure 2:
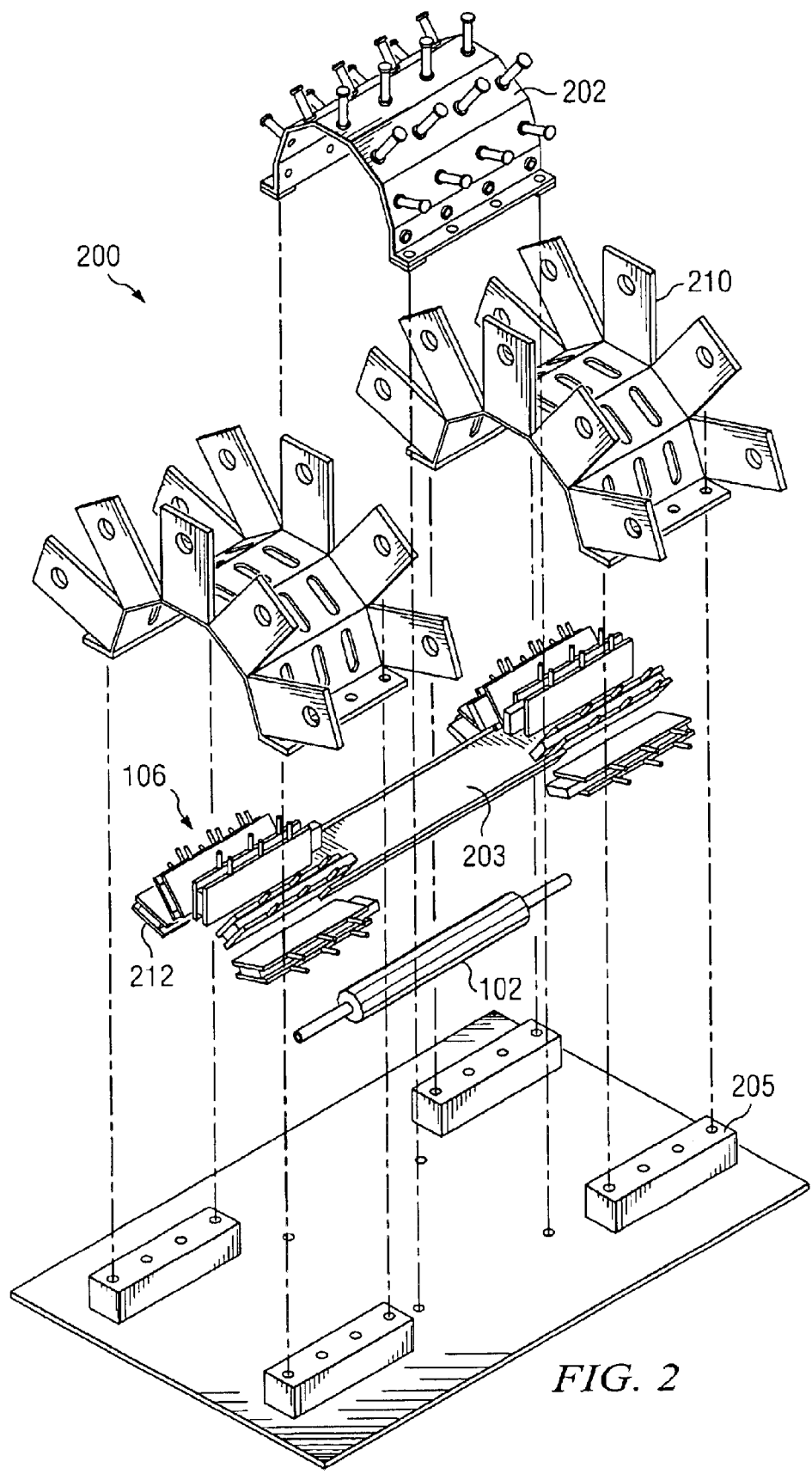
FIG. 2 illustrates an exploded view of a test assembly used for local temperature and/or heat transfer measurements according to one embodiment of the present invention.
Figure 3:
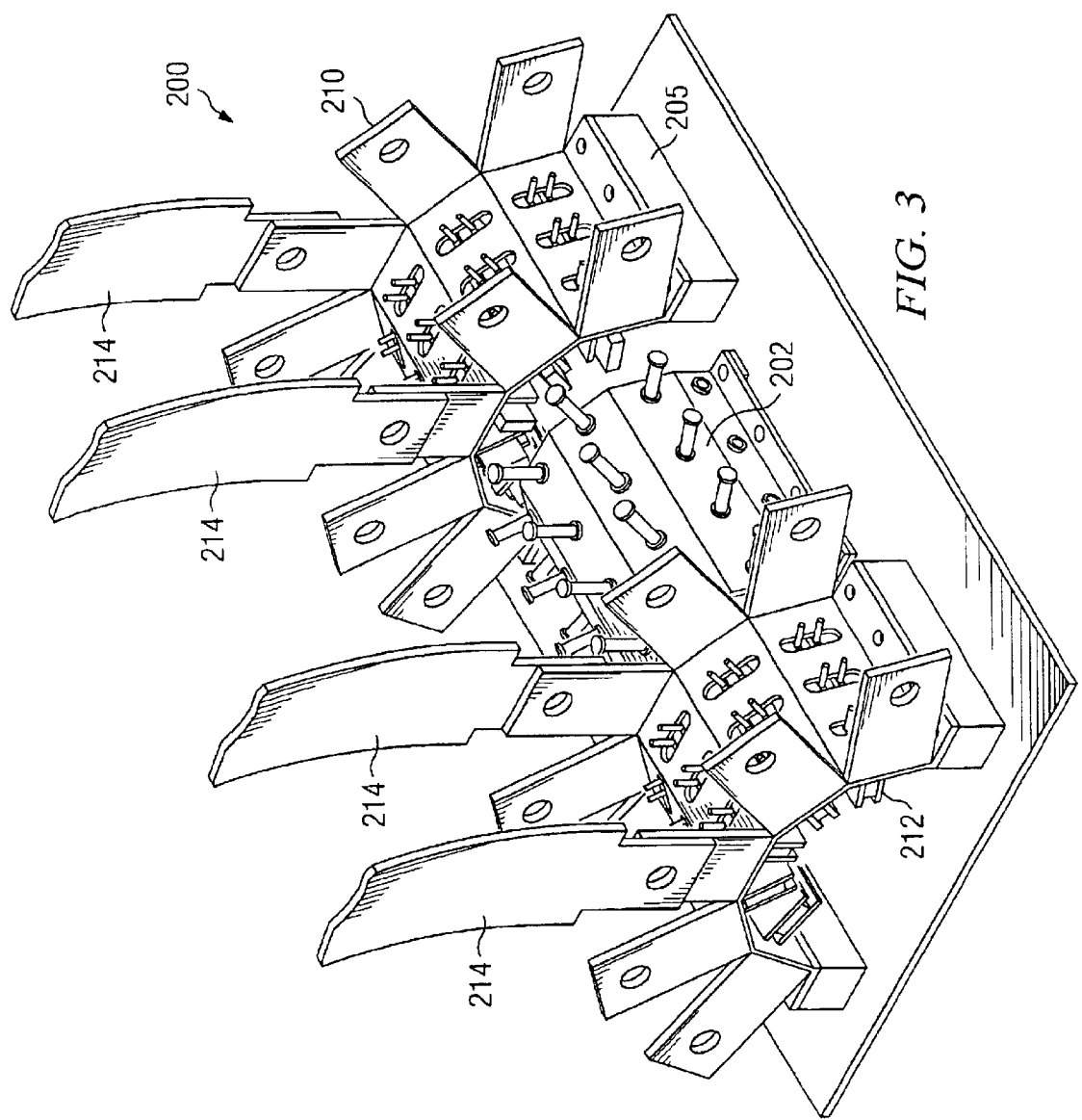
FIG. 3 illustrates the assembled test assembly of FIG. 2 according to one embodiment of the present invention.

Referring now to FIGS. 2 and 3, a test assembly 200 is illustrated in exploded and assembled views, respectively. Heat source 106 (FIG. 1A) may be any suitable heat source operable to produce any suitable heat flux. In the illustrated example embodiment, a 350.0 kW DC power supply, which provides resistive heating to conduit 102 via five grade G-20 graphite flat heaters is utilized. These are shown in FIG. 2 and each are placed over a 1.0 mm thick aluminum nitride layer 203, which in turn rests on each of the five flat sides of conduit 102. The aluminum nitride is used for two important purposes: (1) to electrically isolate conduit 102 from the heaters; and (2) to assure good thermal connection between conduit 102 and the heaters. The heat source provides power to the heater elements in the experimental set-up through a copper bus duct/cabling (bus bar) system, which is connected to the test assembly via the bus bar supports shown in FIG. 3. Based on a post-test examination of conduit 102 and measurements, a revised test matrix resulted which included thirty-one conduit 102 wall thermocouples 109.

The mass velocity and exit pressure of fluid 103 used for the example embodiment illustrated were 0.59 Mg/m²s, and 0.207 MPa ($T_{sat}$=121.3° C.), respectively. Type-J thermocouples with a 0.5 mm diameter were used and calibrated to within ±0.1° C. with a precision calibrator. Other uncertainties include ±0.06 Mg/m²s and ±0.004 MPa for the mass velocity and pressure, respectively. For these test conditions, the basic fluid flow is turbulent (Re=6,900) and highly developing with a reciprocal Graetz number ($Gz^{-1}$) of 4.5×10⁴. Conduit 102 was subjected to successively higher heat fluxes over a period of time by heat source 106. And at each level of heat flux, a quasi-steady state was allowed to occur before the heat flux was increased again. As a result, the experimental data (which includes local temperature, pressure, flow rate, voltage, current, etc.) were recorded as a function of time during the entire course of the experiment. Several quasi-steady states occurred and included flow regimes ranging from single-phase flow up to fully-developed subcooled flow boiling. Consequently, a three-dimensional distribution of the local wall temperature of conduit 102 was measured for each quasi-steady state from single-phase flow to fully-developed subcooled flow boiling.

Referring to FIG. 2, test assembly 200 facilitates flow through conduit 102, heating from one side via heat source 106, and secure positioning of both conduit 102 and the heaters. A saddle 202 is used to: (1) secure the position of the heaters relative to conduit 102; and (2) increase the contact pressure between the heater, the aluminum nitride, and the outside surface of conduit 102. The latter function of saddle 202 is important in reducing the thermal contact resistance between each of these layers.

Saddle 202 and conduit 102 are electrically isolated from the heater by a 0.5 mm thick layer of aluminum nitride. The complete assembly of the exploded components in FIG. 2 is shown in FIG. 3. The mykroy 205 shown serves both as a support for test assembly 200 and as electrical and thermal barriers between a bus bar support 210 and the test bed. Also shown in FIG. 3 are the heater connections to bus bar support 210 via heater transition plates 212. A set of flexible bus bars 214 are used to transfer the electrical current from the rigid copper bus bars to bus bar support 210, to transition plate 212, and then to the heaters.

Generally, an optimal design of single-side heated plasma-facing components (PFCs) and electronic heat sinks (EHSs) is dependent on using conjugate heat transfer to find the local distribution of inside wall heat flux on the flow channels of the component or heat sink cooling substrate. For one physical configuration involving a single-side heated cylindrical-like flow channel with internal forced flow, such as test assembly 200, the local wall heat flux of inside surface 114 and other fundamental convective/flow boiling quantities are obtained from selectively chosen local wall temperatures close to the inside surface of flow channel 104 utilizing thermocouples 109. To this end, three-dimensional thermal measurements for conduit 102 were made. The resulting local wall temperature data were reduced using a theoretical analysis to produce the circumferential and radial distributions. The following fundamental inside channel wall convective and flow boiling thermal quantities were deduced from local channel wall temperature measurements: (1) inside wall heat flux distribution, (2) inside wall temperature distributions, and (3) local heat transfer coefficients.

In the illustrated example embodiment, conduit 102 was based on a theoretical analysis of the two-dimensional (radial, r, and circumferential, $\phi$), wall temperature distribution in a solid circular tube (with inside and outside radii, $r_i$ and $r_o$) with internal forced convective flow and: (1) subjected to an external heat flux ($q_o$) over one-half of the outside perimeter, and (2) with the remaining half of the perimeter insulated. For a constant inside mean heat transfer coefficient ($h_m$), the dimensionless two-dimensional wall temperature distribution is $$T*(R, \phi) = \frac{T(r,\phi) - T_b}{\left(\frac{q_o r_o}{k}\right)} = \frac{1}{2}\left(\frac{1}{Bi} + \ln R\right) + \sum_{n=1}^{\infty} \frac{2 \sin n(\phi + \frac{\pi}{2})}{\pi n^2} \frac{R^n}{R_o^n} \frac{(1 - Bi_n R^{-2n})}{(1 + Bi_n R_o^{-2})}, \quad (1)$$

where n=1, 3, 5, 7, . . . ;

$$R = \frac{r}{r_i}; \quad R_o = \frac{r_o}{r_i};$$

$q_o$ is the externally applied heat flux; k is the wall thermal conductivity; Bi is the Biot number, ($r_i h_m/k$); $\phi=0$ at the heated part of the plane of symmetry; and, $$Bi_n = \frac{Bi - n}{Bi + n}. \quad (2)$$

The corresponding dimensionless inside wall heat flux is $$\frac{q_i(\phi)}{q_o} R_0^{-1} = \frac{1}{2} + \sum_{n=1}^{\infty} \frac{\frac{4 \sin n(\phi + \frac{\pi}{2})}{\pi n R_o^n} x}{\frac{Bi}{[(Bi + n) + (Bi - n)R_o^{-2n}]}}. \quad (3)$$

One result of the analysis is that multi-dimensional wall effects will be negligible for: (1) Bi≦0.01 when $R_o$≧1.34, and (2) Bi≦0.001 when $R_o$=1.04. For these two extrema, the resulting inside channel wall heat flux will not vary in the circumferential direction. For the illustrated experiment, the Bi is anticipated to be of the order of 0.2, which may result in significant circumferential variations of the inside channel wall heat flux. Therefore, the above equations for T(r, $\phi$) and $q_i$ ($\phi$) were applied at a given axial location using the local bulk fluid temperature ($T_b$ (z)) to reduce the measurements of local wall temperature.

The locally measured wall temperature from thermocouples 109 are used in equation (1) to produce a value of Bi, which is henceforth referred to as $Bi_c$ and is then used in equation (1) for R=1 and equation (3) to obtain corresponding values of the inside wall temperature ($T_i$) and heat flux ($q_i$), respectively. The subscript "c" is used here to denote this quantity, $Bi_c$, not as a characterizing Biot number but as a correlation parameter which facilitates extrapolating the measurement over the small distance to the inside boundary. The result is circumferential distributions at a given axial location; i.e., $T_i$ ($\phi$, z) and $q_i$ ($\phi$, z).

Calorimetric measurements were used to measure the actual power transferred to the flowing fluid 103. The actual power transferred to fluid 103 is given in terms of inlet and outlet specific enthalpies by $$P_a = \dot{m}(h_{outlet} - h_{inlet}), \quad (4)$$

where $\dot{m}$ is the mass flow rate, which may be measured by flow measuring device 112 (FIG. 1A) or other suitable methods. The actual external, net heat flux is given by $$q_o = \frac{P_a}{5 A_H}, \quad (5)$$

where $A_H$ is the surface area (180.0 mm×9.04 mm; i.e., $L_H$×w) of one of the heaters, $L_H$ is the heater length and w is the heater width.

The local axial bulk fluid temperature may be determined from thermodynamics tables as the temperature corresponding to the following value of the local axial bulk fluid specific enthalpy; i.e., $$h_b(z) = h_{inlet} + \frac{5.0 q_o z w}{\dot{m}}, \quad (6)$$

where the factor of 5.0 applies to the single-sided heated circular cylinder. In an effort to collapse the measured data on to a single curve, additional definitions of the dimensionless temperature and inside wall heat flux were obtained from eqs. (1) and (3) as follows:

$$\theta_T = \frac{T^* - \frac{1}{2}\left(\frac{1}{Bi_c} + \ln R\right)}{\frac{2}{\pi} \frac{R}{R_o} \frac{(1 - Bi_{nc}|_{n=1} R^{-2})}{(1 + Bi_{nc}|_{n=1} R_o^{-2})}}, \quad (7)$$

$$\theta_q = \frac{\frac{q_i}{q_o} - \frac{R_o}{2}}{\frac{4}{\pi} \frac{Bi_c}{[(Bi_c + 1) + (Bi_c - 1)R_o^{-2}]}}, \text{ and } Bi_{nc} = \frac{Bi_c - n}{Bi_c + n}. \quad (8)$$

Inspection of the reduced data trends indicates that for a given value of Reynolds number, $Bi_c$ is related to $q_o$ ($r_o - r_i$)/k, $\phi$, and z. Equations (7) and (8) were used to express the measured data in a further dimensionless form for the temperature ($\theta_T$) and the inside wall heat flux ($\theta_q$). The resulting data was compared and was collapsed using local values of $T_b(z)$ with the theoretical reduced forms of eqs (1) and (2); i.e., $$\theta_T = \sin(\phi + \frac{\pi}{2}) + \sum_{n=3}^{\infty} \frac{\sin n(\phi + \frac{\pi}{2}) R^{n-1}}{n^2 R_o^{n-1}} x \frac{(1 - Bi_n R^{-2n})}{(1 + Bi_n R_o^{-2n})} \frac{(1 + Bi_n|_{n=1} R_o^{-2})}{(1 - Bi_n|_{n=1} R^{-2})} \quad (9)$$

$$\theta_q = \sin(\phi + \frac{\pi}{2}) + \sum_{n=3}^{\infty} \frac{\sin n(\phi + \frac{\pi}{2})}{n R_o^{n-1}} x \frac{(Bi + 1) + (Bi - 1)R_o^{-2}}{(Bi + n) + (Bi - n)R_o^{-2n}} \quad (10)$$

where n=3, 5, 7, . . .

The above analysis resulted in two-dimensional distributions of the inside flow channel wall temperature, heat flux and heat transfer coefficient. Results are presented below with water as fluid 103 for flow conditions ranging from single-phase to fully-developed subcooled flow boiling. Boiling curves, dimensionless representations, and tabulated reduced data are presented. This data contains the effects of conjugate heat transfer with turbulent and subcooled flow boiling. All the data was reduced, used to compute $\theta_T$ and plotted along with the right-hand side of equation (9). All the data collapsed on to the curve formed from equation (9).

Alternate configurations for conduit 102 and/or test assembly 200 are contemplated by the present invention. One such alternate configuration is shown and described below in conjunction with FIGS. 12A through 18. Other alternate embodiments may also include a different external or applied energy source heat flux. Various embodiments may be accounted for by suitably modifying equations (1) through (5) above.

Figure 4:
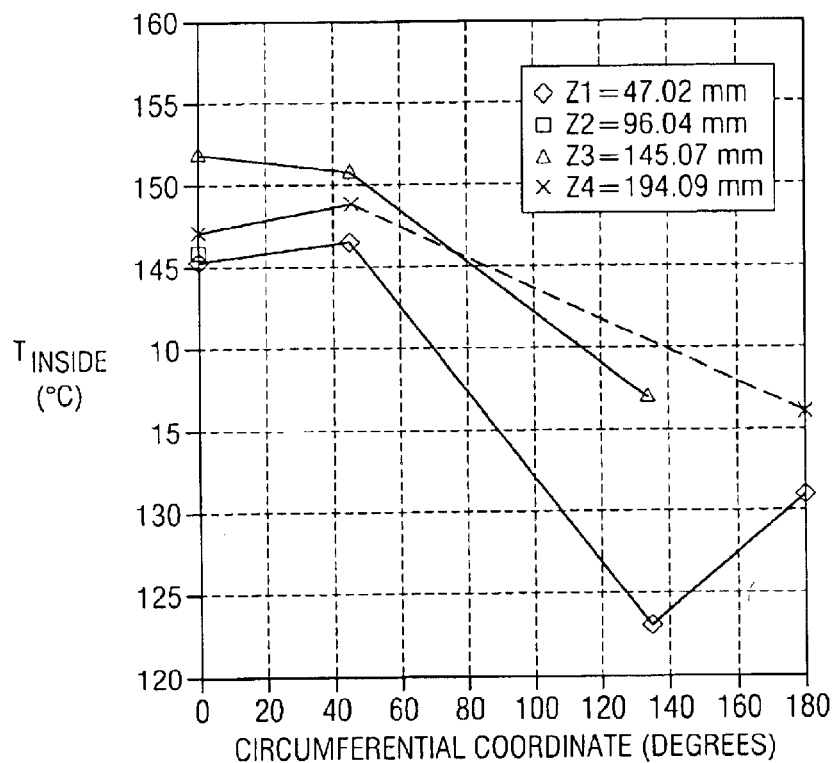
FIGS. 4 and 5 illustrate circumferential variations of the inside circular-like test flow channel wall temperature $T_i$ and dimensionless wall temperature $T^*$, respectively, at different axial locations and derived from measurements made at radial locations about midway between the heated and cooled boundaries for an outside (or incident) single-side heat flux of 728.3 KW/m$^2$.

FIG. 4 shows the circumferential distribution of the inside flow channel wall temperature ($T_i$) at radial locations midway between the heated boundary and the fluid-solid (cooling) boundaries. The plot is for a net incident outside heat flux of $q_o$=728.3 kW/m². For this outside single-side heat flux, the inside wall heat flux is near 1,368.0 kW/m² at z=192.1 mm, and φ=0.0 degrees. At φ=0.0 degrees, $T_i$ increases slightly with z up to the third downstream axial station (z=143.1 mm) and then decreases as the outlet of flow channel 104 is approached. As shown, the slope of the inside wall temperature profile is near zero at φ=0.0 degrees. Since there were at most only four circumferential measurement locations, the circumferential data serve as a guide for the detail distribution. Data interpretation improves when the fact that the slope of the $T_i$-profile must also be zero at φ=180 degrees.

A dotted line is used in all plots between data points to indicate that there is a missing data point entry between those two points that could have otherwise helped to better define the variation between those two points. For example, at z=$Z_4$ in FIG. 4, a dotted line connecting the right-most data points indicates that a missing data point entry is between those two points. If that entry was not missing, more definition in the circumferential variation would have existed and could have been used possibly to verify the zero-slope condition and better display the variation in $T_i$ as φ=180.0 degrees is approached. This may be illustrated further by the data at z=$z_1$, where all four circumferential data entries are present. While the zero-slope condition at φ=0.0 degrees is apparent, a similar condition at φ=180.0 degrees is only realized when it is realized that the shown right-most two data points represent bounds for the physical profile as 180.0 degrees is approached. Each point in FIG. 4 is for a slightly different radial location. The exact radial and other coordinate location for each point is also contained in the tabulation.

Figure 5:
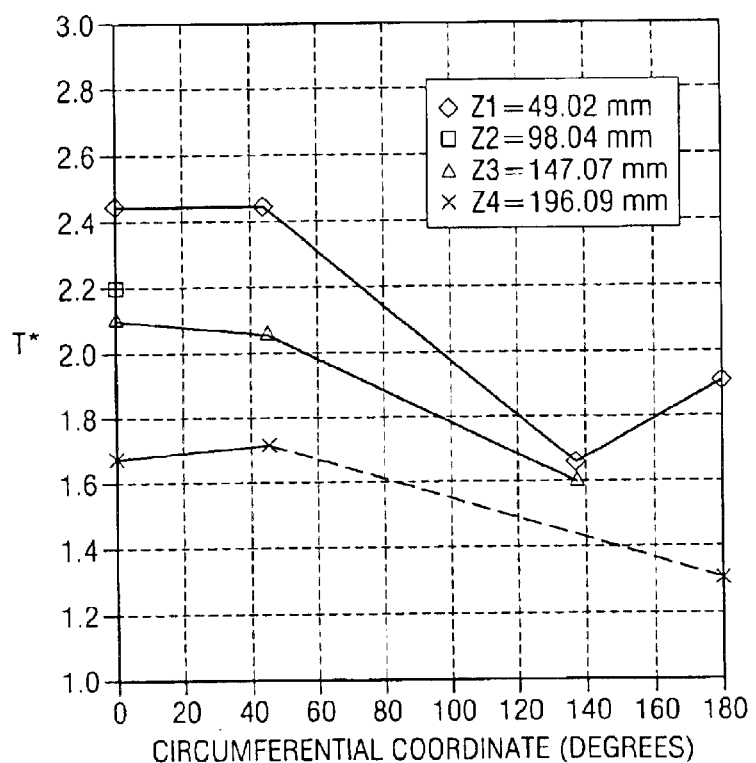

The non-dimensional form of $T_i$ is T* and is presented in FIG. 5. The non-dimensionalization reverses the relative magnitudes of the ordinate (compare FIGS. 4 and 5). The representation puts the data points in a form that would be conducive for comparisons with other conjugate heat transfer/flow boiling predictive tools.

Figure 6:
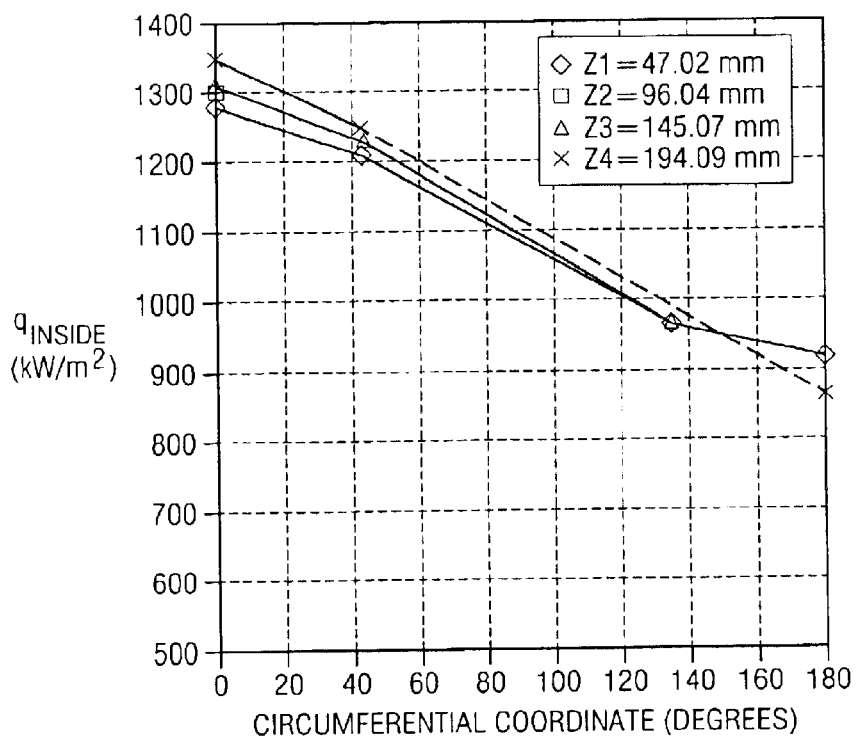
FIGS. 6 and 7 illustrate circumferential variations of the inside circular-like test section flow channel wall heat flux ($q_i$) and dimensionless wall heat flux ($q_i/q^{o*}R_o^{-1}$), respectively, at different axial locations and derived from measurements made at radial locations about midway between the heated and cooled boundaries for an outside (or incident) single-side heat flux of 728.3 kW/m$^2$.
Figure 7:
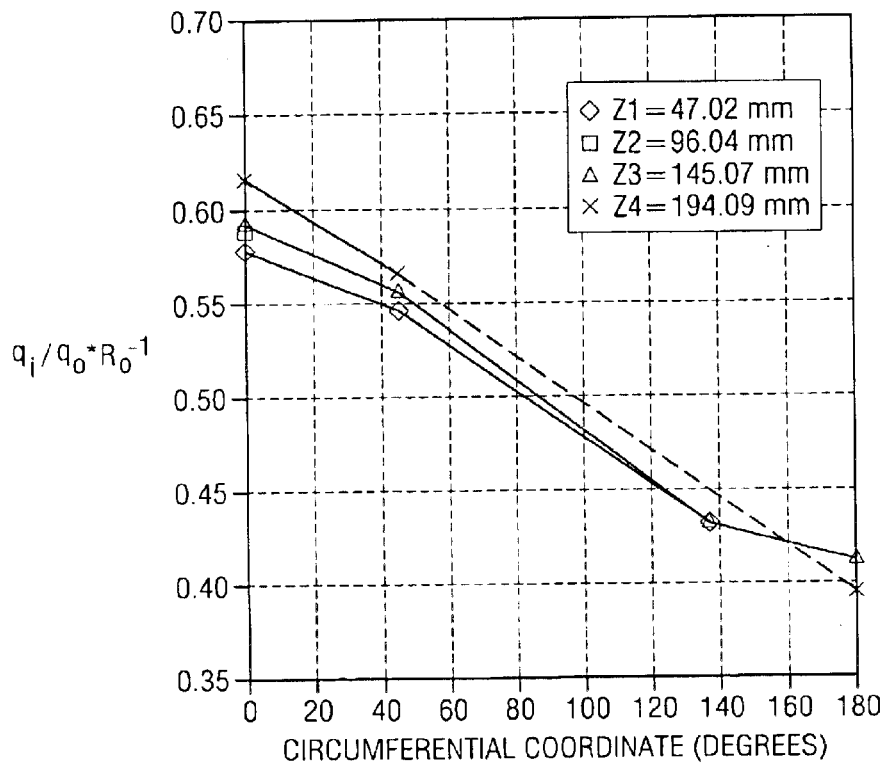

Referring to FIG. 6, the data representing the circumferential, inside wall heat flux ($q_i$) profile is shown for the above noted conditions. The variations with respect to φ are substantial and can be seen to be amenable to the zero slope conditions at φ=0.0 and 180.0 degrees. At φ=0.0 degrees, $q_i$ increases with z. All thirty-one thermocouple 109 data were reduced to produce values of $q_i$. For a given value of φ and z, the thermocouples closest to the heated boundary resulted in higher values of $q_i$ than the other two locations close to fluid 103. It is believed that those locations closest to the fluid boundary result in better estimates of $q_i$. The reduced data for $q_i$ and $T_i$ and the data for T (r, φ, z) form an evolving conjugate heat transfer database with influences of turbulence, developing flow, single-side heating, single-phase flow, and flow boiling. The corresponding values of the local (axial) bulk fluid (water) temperature are also tabulated. The representation of the inside heat flux in dimensionless form is given in FIG. 7.

Figure 8:
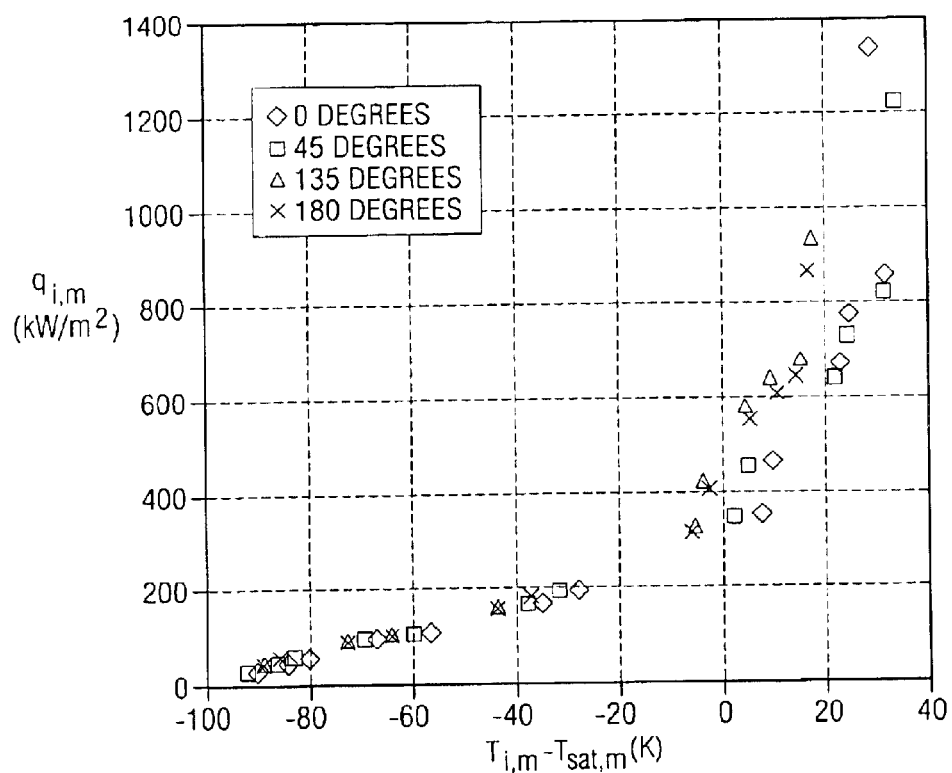
FIGS. 8 through 11 are example flow boiling curves according to one embodiment of the present invention.
Figure 9:
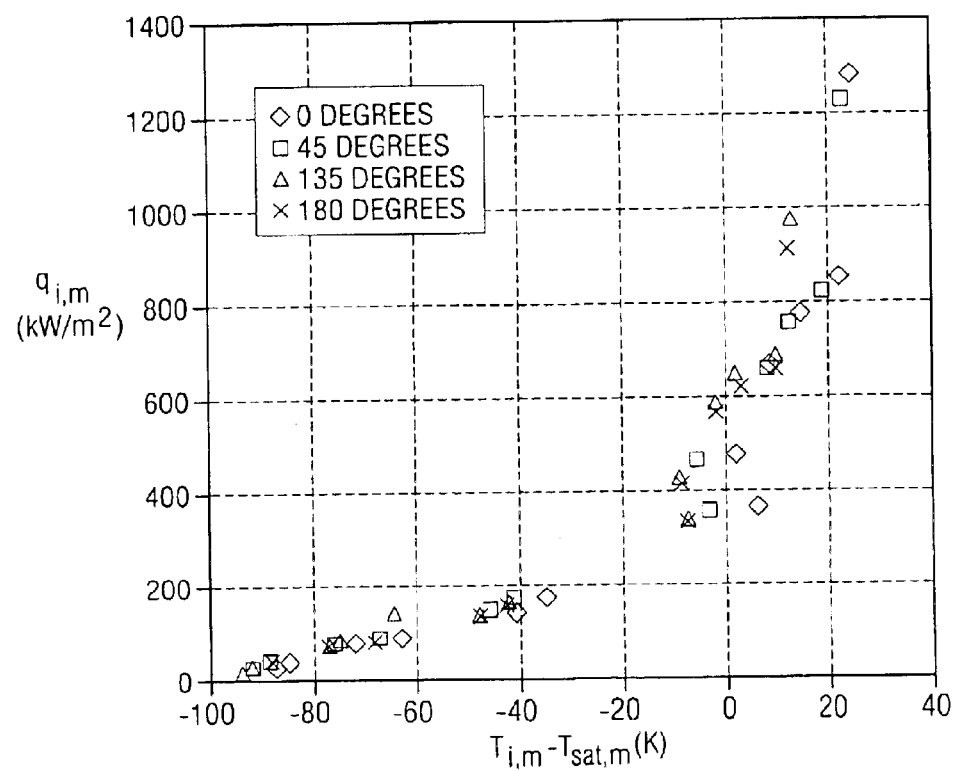
Figure 10:
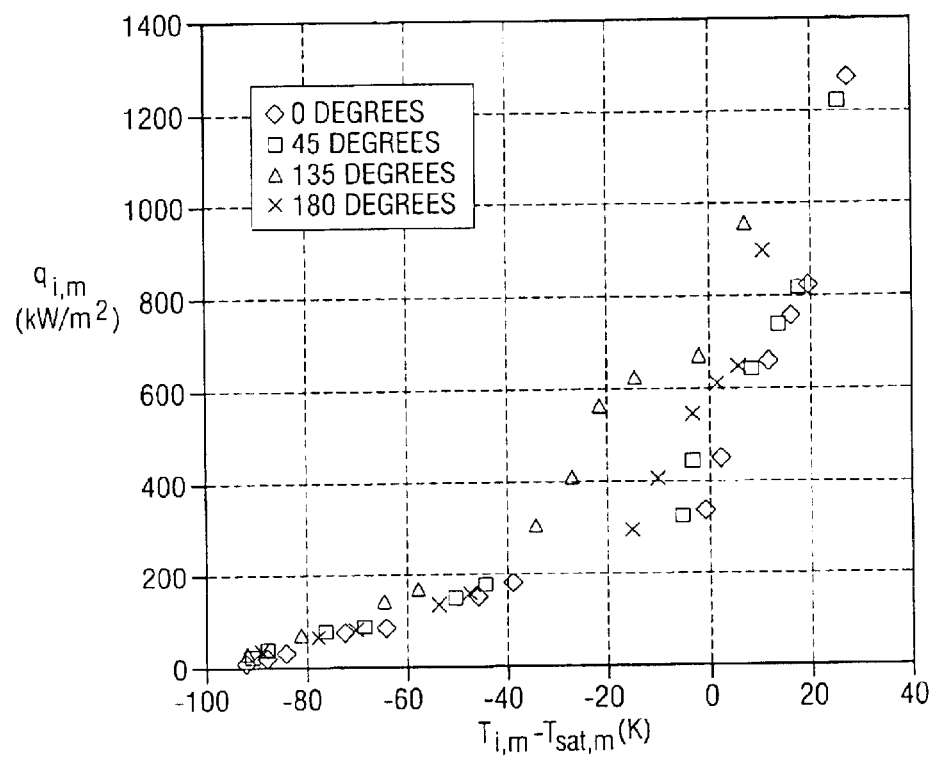
Figure 11:
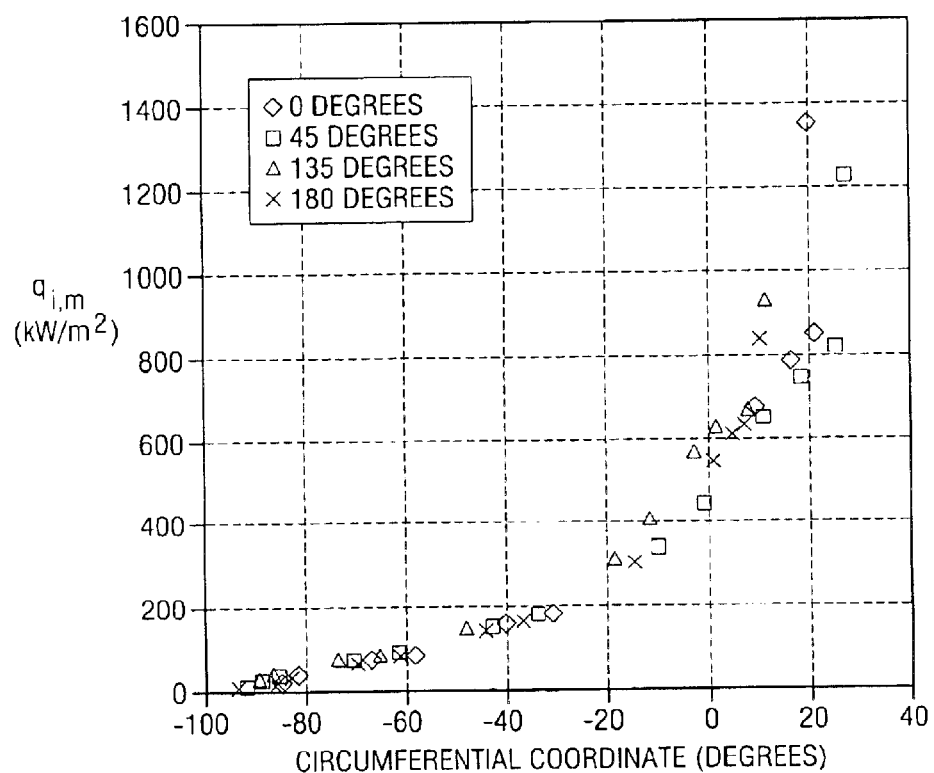

Two-dimensional (circumferential and axial), local boiling curves are presented for subcooled water flow boiling in a single-side heated circular flow channel. Although a complete compilation of all the reduced data is contained in the above noted tabulations, examples of the 2-D boiling curves are shown in FIGS. 8 through 11. In these figures, $T_{i,m}$ is the mean value of $T_i$ at a given value of φ and z. The boiling curves in FIG. 8 are for a nominal axial coordinate of z=$z_3$=143.07 mm.

The quantitative differences in the circumferential (φ) variations of the boiling curve are shown in FIG. 8 for φ varying from 0.0 degrees to 180.0 degrees. The highest two heat fluxes (right-most pair of points) at 0.0 degrees indicate a fully developed boiling regime exists; and as φ increases, the slope of the boiling curve at similar points decreases which indicates that a region of less and less partially developed flow exists. Although these trends exist at all axial locations, the circumferential variations did change for different values of z.

The axial variations can be discerned by comparing FIGS. 8 through 11. As one would expect, the superheat (i.e., $T_i-T_{sat}$) and the above noted slopes at all circumferential locations decrease with z. As z decreases from $z_3$=143.07 mm (FIG. 8) to a nominal axial location of z=$z_2$=94.04 mm (FIG. 9), there is a change in the polarity of the relative superheat for φ=0.0 degrees and 45.0 degrees at the highest heat fluxes. As z decreases further to 45.0 mm (FIG. 10), the polarity remains unchanged and the absolute value of the differences in relative superheat increases. However if z increases from $z_3$ to z=$z_4$=192.09 mm (FIG. 11), the polarity does not change; but, the differences in the absolute value of the relative superheat increase. The above noted differences may be due to a redistribution of the flow and/or heat transfer. At values of $q_i$ above those shown in FIGS. 8 through 11, a loud hammer-like sound occurred and increased in amplitude as the heat flux was increased.

Thus, high heat flux removal from PFCs and EHSs involves conjugate heat transfer analysis of the applicable substrate and flowing fluid. For the above described case of subcooled flow boiling inside a single-side heated circular channel, the dimensional results show the significant radial, circumferential and axial variations in all thermal quantities for the present radial aspect ratio ($R_o$=outside radius to inside radius) of 3.0. A unified, dimensionless representation of the two-dimensional inside wall heat flux, and the dimensional inside wall heat flux ($q_i$ (φ, z)) and temperature ($T_i$ (φ, z)) data was found and used to collapse the data for all circumferential locations. For an incident heat flux of 728.3 kW/m² and a Reynolds number of 6,900, the inside channel heat flux and heat transfer coefficient at the heated part of the plane of symmetry were 1350.0 kW/m² and 22.5 kW/m²K, respectively. At the cooler part of the plane of symmetry for the same incident heat flux, these thermal quantities were 896.0 kW/m² and 19.9 kW/m²K, respectively. For applications requiring $R_o$<3.0, these differences will increase. 2-D boiling curves are presented and are among the first full set of 2-D boiling data presented for a single-side heated circular configuration.

Figure 12A:
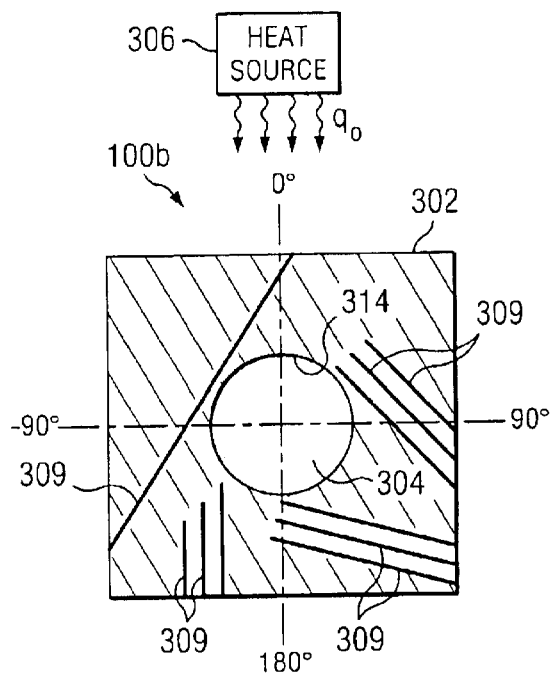
FIG. 12A is an elevation view of another conduit used for local temperature and/or heat transfer measurements according to another embodiment of the present invention.
Figure 12B:
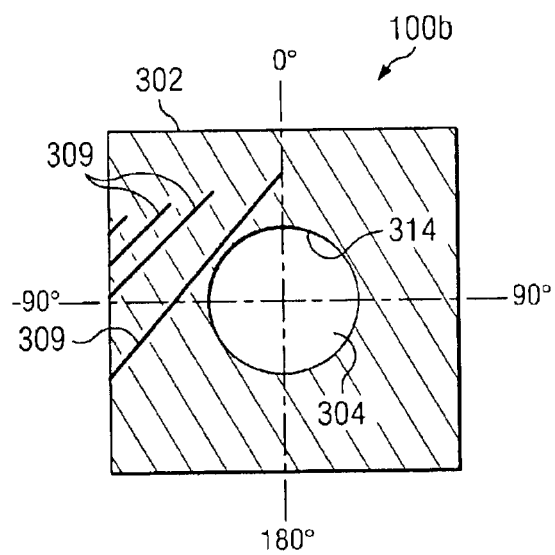
Figure 12C:
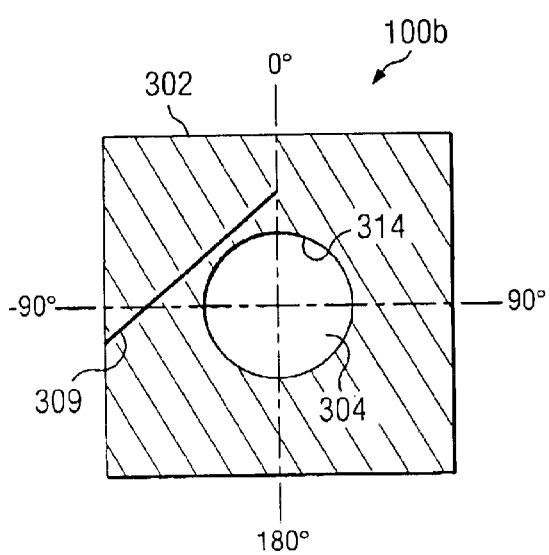

Referring now to FIGS. 12A through 12C, system 100b includes a conduit 302 having a fluid 303 flowing through a flow channel 304. An elevation view of conduit 302 is substantially similar to conduit 102 in FIG. 1A; therefore, all that is illustrated in FIGS. 12A through 12C are three cross-sections at one axial station of conduit 302. Accordingly, in the illustrated example embodiment, conduit 302 has a generally square cross-section and is being non-uniformly heated by a heat source 306. System 100b also includes a computer (not explicitly shown) coupled to a plurality of temperature measuring devices 309 that are disposed within the wall of conduit 302, a pair of fluid thermocouples (not explicitly shown) that are disposed within fluid 103 at the inlet and outlet, respectively, and a flow measuring device (not explicitly shown).

As illustrated below in conjunction with FIGS. 12A through 18, system 100b is utilized within the teachings of another example embodiment of the invention to obtain two-dimensional distributions of wall temperature, heat flux and heat transfer coefficient of an inside surface 314 of flow channel 304. The two-dimensional temperature gradient of fluid 303 may also be obtained. Results of this example embodiment are presented below with water as fluid 303 for flow conditions ranging from single-phase to fully-developed subcooled flow boiling. Boiling curves, dimensionless representations, and tabulated reduced data are presented below.

For the example embodiment illustrated, the overall length of conduit 302, including the inlet and outlet reduced diameter sections, is 360.0 mm. The main section of conduit 302 (available for heating) is 200.0 mm long with a nominal outside width and height of 30.0 mm and an inside diameter of 10.0 mm. The actual directly heated length, $L_H$, was 180.0 mm. Similar to FIGS. 1B through 1D above, FIGS. 12A through 12C, which represent one axial station of conduit 302 includes twelve thermocouples 309, ten of which are shown in FIG. 12A, one of which is shown in FIG. 12B, and one of which is shown in FIG. 12C. The planes illustrated by FIGS. 12B and 12C are axially displaced upstream from the plane illustrated by FIG. 12A by 2.0 mm and 4.0 mm, respectively. Finally, the lengths $L_i$ and $L_o$ (see FIG. 1A) are variable lengths whose sum should equal 20.0 mm for a given experimental setup.

Figure 13:
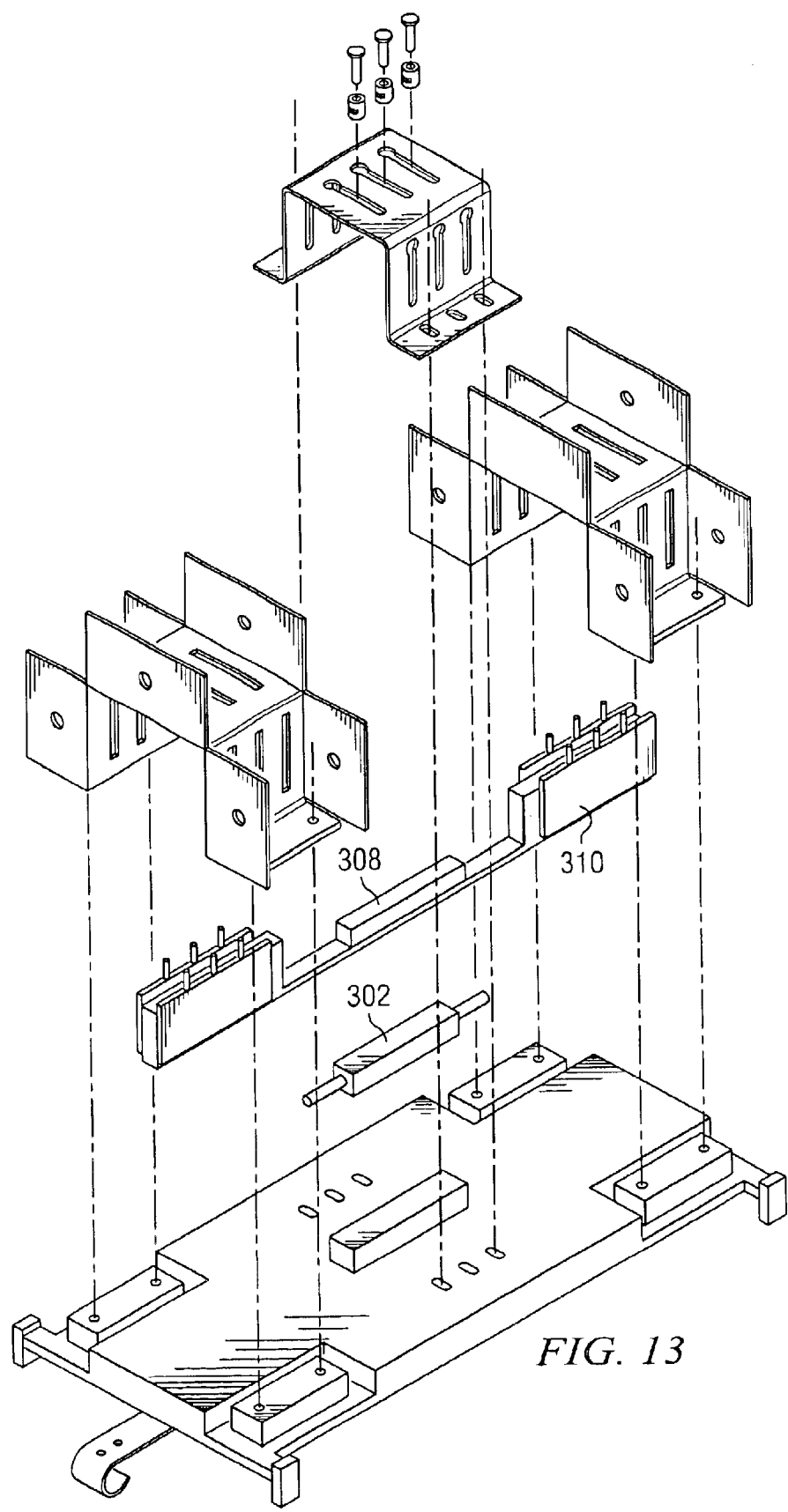
FIG. 13 illustrates an exploded view of another test assembly used for local temperature and/or heat transfer measurements according to another embodiment of the present invention.
Figure 14:
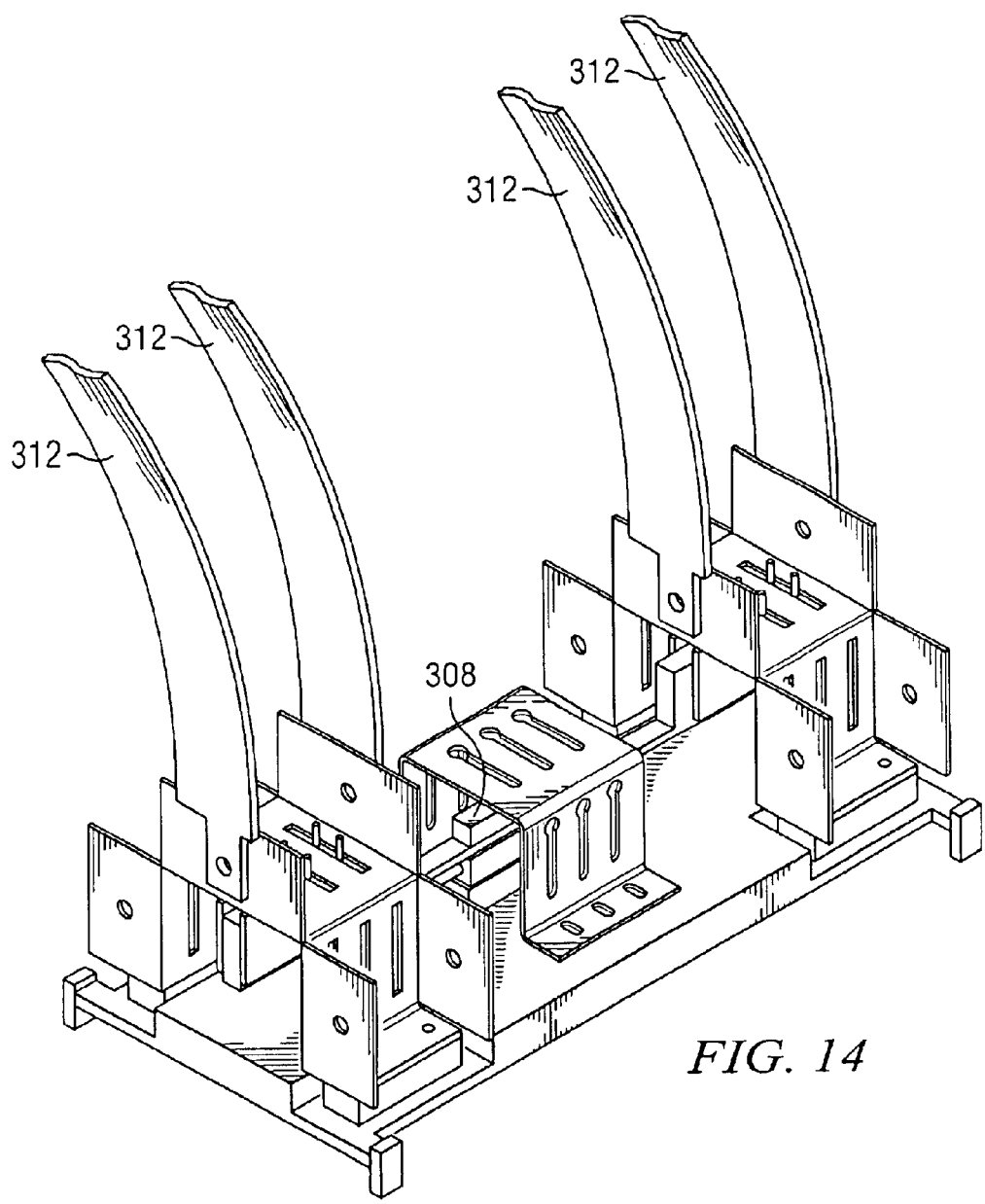
FIG. 14 illustrates the assembled test assembly of FIG. 13 according to one embodiment of the present invention.

Thermocouples 309 in FIGS. 12A through 12C give both radial and circumferential distributions of the local wall temperature. Hence, a combination of all axial stations produces a three-dimensional distribution (i.e., temperature topology) of conduit 302 local wall temperature as a function of the applied heat flux and the water flow regime, which will vary from single-phase at the inlet to subcooled pre- or post-CHF at the outelet. In the illustrated example, heat source 306 is a 350.0 kW DC power supply that provides resistive heating to conduit 302 via one grade G-20 graphite flat heater, which is shown in FIGS. 13 and 14 and was placed over a 1.0 mm thick aluminum nitride layer 308, which in turn rests on conduit 302. The power supply provides power to a heater element 310 (FIG. 13) in the experimental set-up through a copper bus duct/cabling (bus bar 312—see FIG. 14) system.

As described above, robust PFC designs should be based on accurate three-dimensional conjugate flow boiling analyses and optimizations of the PFC local wall temperature and, hence, on the local flow boiling regime variations. Such analyses should have 3-D data as a basis for comparison, assessment, and flow boiling correlation adaptation for localize boiling. Selected results are presented for the example embodiment illustrated in FIGS. 12A through 14 for the: (1) 3-D variations of the wall temperature as functions of the circumferential ($\phi$), radial (r), and axial (Z) coordinates; (2) outside steady-state heat flux as a function of the local wall temperature; and, (3) occurrence of pre- and post-CHF. The outside net incident heat flux relationship with the locally measured wall temperature is discussed first and then compared with similar results for conduit 102 (FIGS. 1A through 11).

Results are presented here that show the relationship, at different radii, between the incident heat flux ($q_o$) and the local wall temperature ($T_w$). Although not identical, this relationship between $q_o$ and $T_w$ is directly related to the two-dimensional local boiling curve if the radius at which this relationship is considered is equal to the inside radius of flow channel 304.

Figure 15:
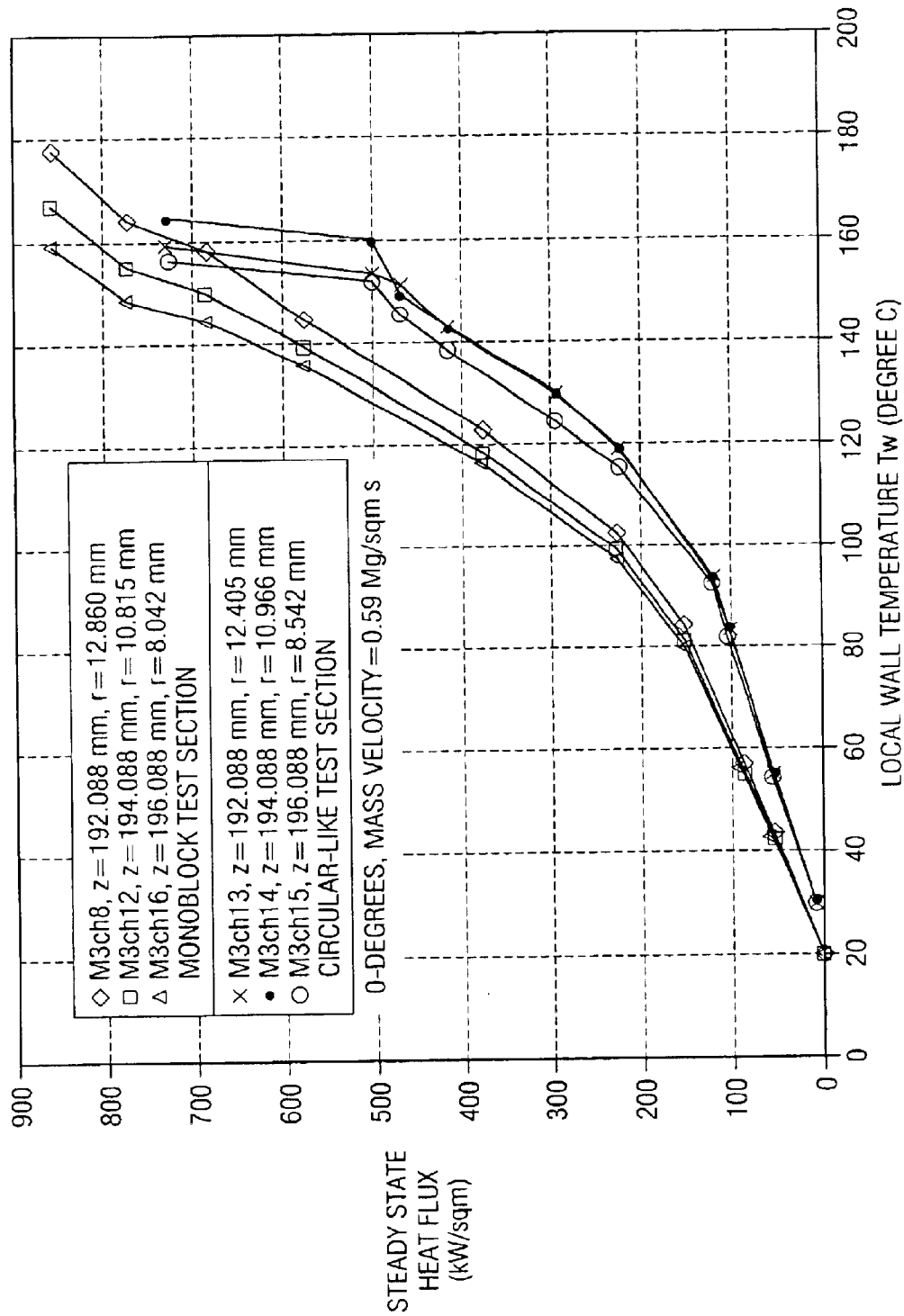
FIG. 15 illustrate comparisons between a single-side heated square conduit and a single-side heated circular conduit using the steady-state net incident (outside) heat flux as a function of the local flow channel wall temperature at $\phi=0.0$ degrees and for specified axial locations (near $Z=Z_4=196.1$ mm) and heaters asymmetrically placed with respect to the axial direction with $L_o=4.0$ mm and $L_i=16.0$ mm for unheated flow channel downstream and upstream of the heaters, respectively.

The relationship between the steady state, net incident outside wall heat flux, $q_o$, and the locally measured conduit 302 wall temperature is presented in FIG. 15 and applies for the following conditions: (1) the 180.0 mm length (=$L_H$) heater was placed asymmetrically along the axial 200.00 mm length of conduit 302, with a 4.0 mm (=$L_o$) unheated length at the downstream end of conduit 302, and a 16.0 mm (=$L_i$) unheated length at the upstream end of conduit 302; (2) $\phi$=0.0 degrees at the heated side of the axis of symmetry; (3) axial locations of Z=143.1, 145.1, and 147.1 mm (nominally, Z=$Z_3$=147.1 mm axial station); and (4) radii of 12.82, 10.62, and 7.95 mm, respectively. For the results reported below, the test conditions used for the mass velocity and exit pressure were 0.59 Mg/m²s and 0.207 MPa ($T_{sat}$= 121.3° C.), respectively.

The results are presented for conduit 302 and are later compared with similar results for conduit 102. These curves in FIG. 15 are complete in that they not only show evidence of an influence from the three basic subcooled flow boiling regimes prior to CHF (single-phase, partially nucleate boiling, and fully developed flow boiling); but an apparent local CHF occurred and is displayed in FIG. 15 between the right-most pair of similar data points on a given curve for conduit 302. For each curve (or radial coordinate) shown in FIG. 15, the four left-most similar data points on a given curve (or radius) show the relationship when single-phase convection exists in flow channel 304. Beyond the point of highest heat flux for this group of four similar points, the onset of partial nucleate boiling occurs and extends up to the next four similar points.

Finally and beyond the heat flux of the latter points at each radius (or on each curve) to the next similar data point, one observes a progressive increase of the slope of the $q_o$ vs $T_w$ curves in FIG. 15 as the radius decreases or as the inside fluid-solid boundary is approached. This denotes the region of fully developed nucleate flow boiling in flow channel 304. The occurrence of a local CHF is denoted by a decrease in the slope of the curves as $q_o$ increases further. The reduction in the slope at the upper part of these curves for conduit 302 in FIG. 15 suggests a stable entry into the local post-CHF regime at $\phi$=0.0 degrees and Z=$Z_4$ (which is nominally 196.1 mm) occurred and is displayed between the right-most pair of similar data points for a given radius (or for a given curve) for conduit 302. As the heat flux was increased above that at these latter pairs of similar data points, a loud hammer-like sound also began and increased in amplitude as the heat flux was further increased. In addition, moderate local wall temperature fluctuations (about 10° C.) begin with a modest increase in the incident heat flux (850 to 870 kW/m²). These periodic fluctuations increased in magnitude to about 18.0° C. as $q_o$ was increased to near 1.08 MW/m². Although these data characterizing periodic steady conditions are not plotted in the steady-state plot in FIG. 15, it interesting to note that these periodic steady conditions resulted in an increase in the slope of the $T_w$-$q_o$ curve and, hence, resulted in locally stable, steady, periodic conditions in which the local mean or peak wall temperature was almost constant. The normal temperature escalation, which accompanies CHF in uniformly heated tubes, was absent due to the single-side heated flow channel 304 and the resulting three-dimensional conjugate heat transfer (which is absent in the uniformly heated cases). This escalation may occur when a global CHF is reached.

FIG. 15 shows a comparison of two single-side heated geometries: (1) conduit 302 heated on one of its four outside surfaces, and (2) conduit 102 heated on one-half of its outside circumference. For this comparison, the mass velocity was 0.59 Mg/m²s and the measurements were made near the end of the heated length of the conduits. The cross-sectional aspect ratio (RE) for conduit 302 is defined as the ratio of the width of conduit 302 to the inside diameter of flow channel 304. Further, $R_o$ for conduit 102 is the ratio of the outside diameter to the inside diameter. For both of these cases, $R_o$ is 3.0. As expected at a given level of heat flux, the local wall temperature in conduit 102 are typically higher than those in conduit 302. Correspondingly at a given power level, the local conduit 302 wall temperature is higher than that for conduit 102. Further, the fully-developed flow boiling region extended over a broader heat flux range for conduit 102 when compared with conduit 302. Near the fluid-solid boundary, the on-set to fully-developed boiling occurred at a slightly higher temperature for conduit 102 than for conduit 302.

Figure 16A:
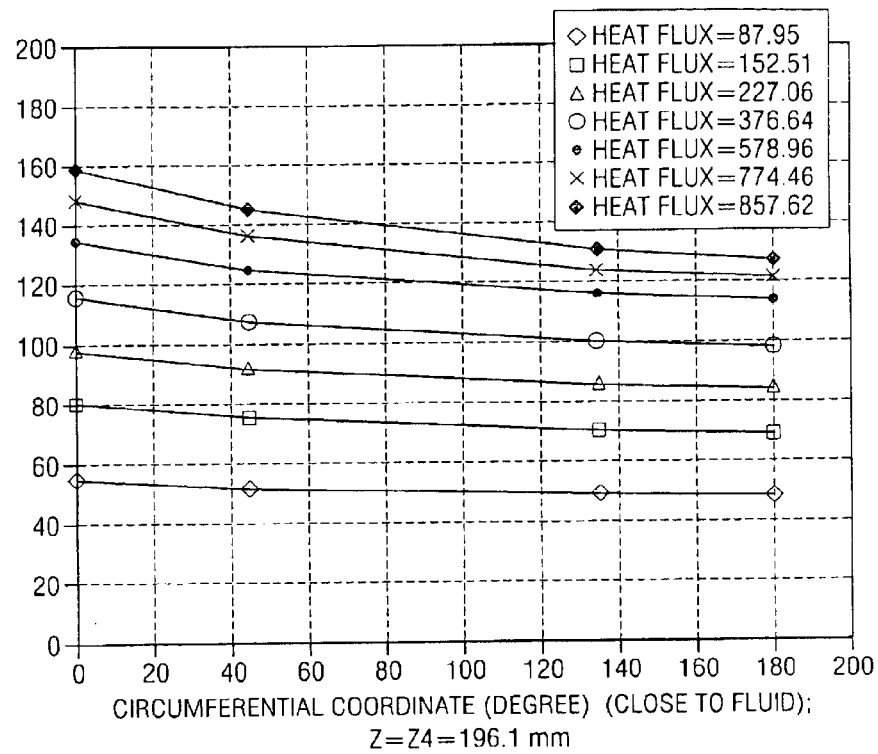
FIG. 16A illustrates a circumferential wall temperature profile from the thermocouples nearest to the fluid/solid boundary as a function of net incident heat flux, at $Z=Z_4=196.1$ mm ($L_o=4.0$ mm, and $L_i=16.0$ mm) according to one embodiment of the present invention.
Figure 16B:
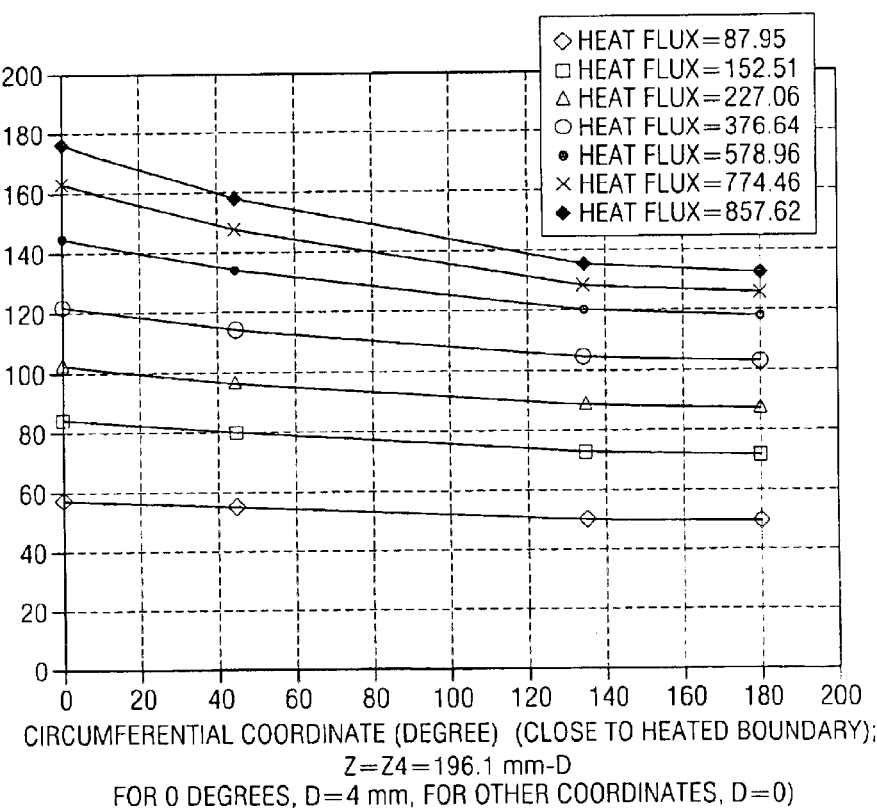
FIG. 16B illustrates a circumferential wall temperature profile from the thermocouples nearest to the heated boundary as a function of the net incident heat flux ($L_o=4.0$ mm, and $L_i=16.0$ mm) according to one embodiment of the present invention.

The circumferential variations in conduit 302 channel wall temperature are presented in FIGS. 16A and 16B for eight levels of the outside, single-side heat flux, $q_o$. FIGS. 16A and 16B show such variations close to the inside fluid-solid boundary and the outside (partially heated) boundaries, respectively. Comparing the two sets of plots, one observes that the circumferential wall temperature variations have some clear differences (which will increase as the channel wall thickness decreases) but are basically similar near the two boundaries. Since there are only four circumferential locations for each set of measurements, these distributions do not show the exact local circumferential slopes but the quantitative trends at the four locations are evident. The locus of the data in FIGS. 16A and 16B displays approximately the correct boundary condition of a zero circumferential temperature gradient as φ approaches both 0.0 and 180.0 degrees. Close to the fluid-solid boundary, the temperature is almost constant between φ=135 and 180 degrees. As φ increases near both boundaries, the local wall temperature decreases sharply and then gradually as expected. The gradual decrease is due to the large value of $R_o$. As $R_o$ decreases, this circumferential variation will increase. In all cases, the local wall temperature increases with $q_o$.

At all heat flux levels, the temperature variations between φ=0 and 45 degrees are usually much less for conduit 102 than for conduit 302. This implies that for a given heat flux level above that needed for local boiling, a larger portion of the conduit 102 inside wall experiences boiling in the circumferential direction than conduit 302.

Figure 17:
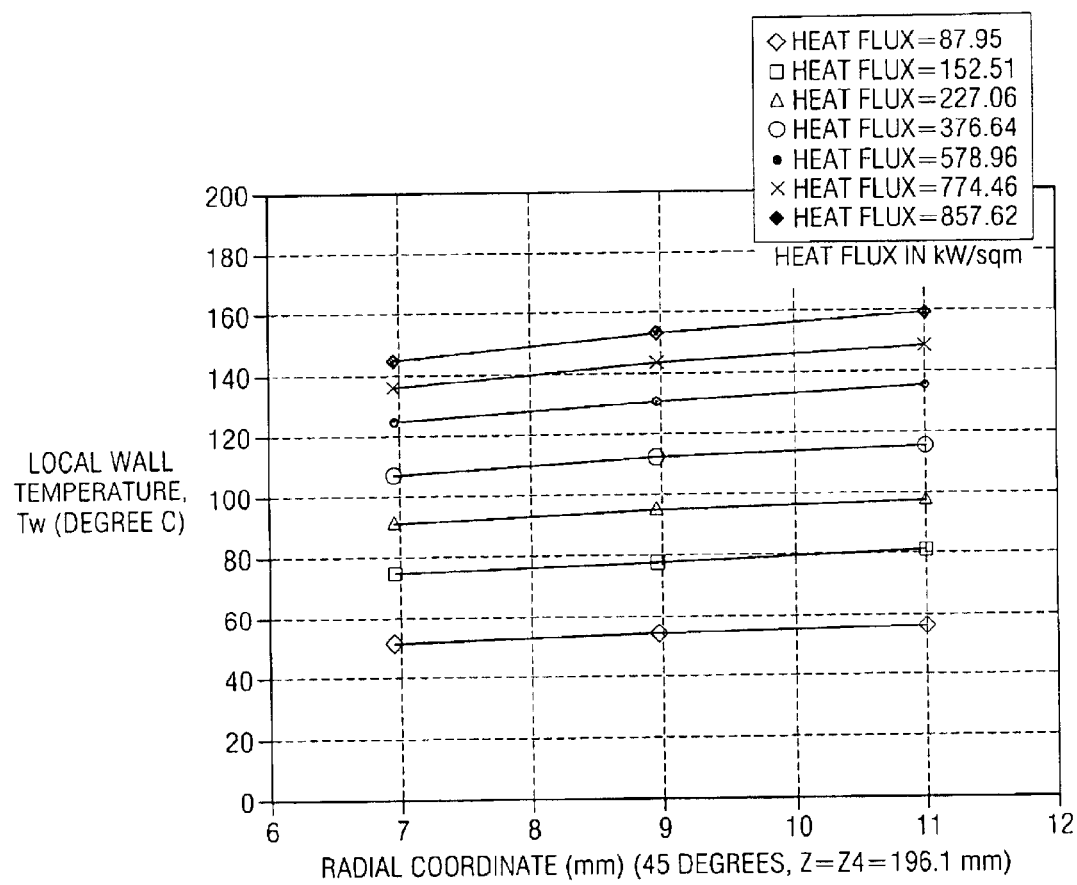
FIG. 17 illustrates a radial wall temperature profile for the monoblock flow channel at $\phi=45.0$ degrees and $Z=Z_4=196.1$ mm as a function of the net incident heat flux ($L_o=4.0$ mm, and $L_i=16.0$ mm) according to one embodiment of the present invention.

FIG. 17 displays the radial temperature profiles at φ=45.0 degrees and shows small variations with respect to r and some values of φ when compared with the radial dependence in FIGS. 16A and 16B. As can be seen from FIGS. 16A and 16B, the radial variation at φ=0 degrees is larger than at other circumferential locations. These radial temperature profiles may be useful in estimating the local heat flux and wall temperature on inside surface 314 of flow channel 304.

Finally, FIG. 18 shows the remaining portion of the 3-D variations via the axial wall temperature profiles. For present work, the heater length ($L_H$) was 180.0 mm long (in the axial direction) and was placed asymmetrically on conduit 302 (200.00 mm long). There was 16.0 mm (=$L_i$) of unheated (i.e., directly unheated) conduit 302 upstream of the heater and near the inlet, and 4.0 mm (=$L_o$) of unheated (i.e., directly unheated) conduit 302 downstream of the heater near the outlet. This resulted in the downstream portion of the heater being at the same downstream axial location as thermocouples 309 illustrated in FIG. 12A. As a result, thermocouples 309 at the downstream most axial location are in the same axial plane as the downstream end of the heater. The curves shown in FIG. 18 are for conduit 302 locations along the heated portion of the axis of symmetry (φ=0.0 degrees) and close to the heated boundary. This local axial wall temperature profile along the heated boundary and at φ=0.0 degrees shows that the wall temperature in the axial direction increases with the axial coordinate up to the third axial station ($Z=Z_3$=147.1 mm), beyond which the local wall temperature decreases. Although small axial variations occurred between $Z_2$ (=98.0 mm) and $Z_3$ (=147.1 mm) at all power levels, these variations would increase for conduit 302 wall and prototype PFC substrate thicknesses smaller than the 10.0 mm nominal value for the present case.

PFCs for fusion reactors and other high heat flux heat sinks are usually subjected to a peripherally non-uniform heat flux. The configuration studied above in conjunction with FIGS. 12A through 18 is related to these applications and include a single-side heated conduit with a circular coolant channel bored through the center. The results include three-dimensional conduit 302 wall temperature distributions and a clear display of both critical heat flux (CHF) and post-critical heat flux for a single-side heated configuration. These results are very encouraging in that they are among the first full set of truly three-dimensional conduit 302 wall temperature measurements for a one-side heated flow channel that contains the effects of conjugate heat transfer for turbulent, subcooled flow boiling.

Although embodiments of the invention and their advantages are described in detail, a person skilled in the art could make various alterations, additions, and omissions without departing from the spirit and scope of the present invention.

What is claimed is:

1. A method, comprising:
   providing a conduit having a fluid flowing there through;
   disposing a plurality of temperature measurement devices inside a wall of the conduit;
   positioning at least some of the temperature measurement devices proximate an inside surface of the wall of the conduit;
   positioning at least some of the temperature measurement devices at different radial positions at the same circumferential location within the wall;
   measuring a plurality of temperatures of the wall with respective ones of the temperature measurement devices to obtain a three-dimensional temperature topology of the wall;
   determining the temperature dependent thermal conductivity of the conduit; and
   determining a multi-dimensional thermal characteristic of the inside surface of the wall of the conduit based on extrapolation of the three-dimensional temperature topology and the temperature dependent thermal conductivity.

2. The method of claim 1, wherein determining the multi-dimensional thermal characteristic comprises determining a two-dimensional temperature.

3. The method of claim 1, wherein determining the multi-dimensional thermal characteristic comprises determining a two-dimensional heat flux.

4. The method of claim 1, wherein determining the multi-dimensional thermal characteristic comprises utilizing an inverse conduction computer code to determine the multi-dimensional thermal characteristic.

5. The method of claim 1, wherein determining the multi-dimensional thermal characteristic comprises:
   determining a two-dimensional temperature distribution of the inside surface of the wall of the conduit by solving a dimensionless equation of a generalized form of:

$$T^*(R, \phi) = \frac{T(r, \phi) - T_b}{\left(\frac{q_o r_o}{k}\right)} = \frac{1}{2}\left(\frac{1}{Bi} + \ln R\right) + \sum_{n=1}^{\infty} \frac{2\sin n\left(\phi + \frac{\pi}{2}\right)}{\pi n^2} \frac{R^n}{R_o^n} \frac{(1 - Bi_n R^{-2n})}{(1 + Bi_n R_o^{-2})},$$

where n=1, 3, 5, 7, . . . ;

$$R = \frac{r}{r_i}; R_o = \frac{r_o}{r_i};$$

$r_i$ is the radius of the inside surface of the wall; $r_o$ is the outside surface of the wall; $q_o$ is the known heat flux; k is the thermal conductivity; Bi is the Biot number, $(r_i h_m / k)$; $h_m$ is the mean heat transfer coefficient of the inside surface; $\phi = 0$ at the heated part of the plane of symmetry; and, $$Bi_n = \frac{Bi - n}{Bi + n}$$

6. The method of claim 1, wherein determining the multi-dimensional thermal characteristic comprises:
   determining a two-dimensional heat flux of the inside surface of the wall of the conduit by solving a dimensionless equation of a generalized form of:

$$\frac{q_i(\phi)}{q_o} R_o^{-1} = \frac{1}{2} + \sum_{n=1}^{\infty} \frac{\frac{4\sin n\left(\phi + \frac{\pi}{2}\right)}{\pi n R_o^n} x}{\frac{Bi}{[(Bi + n) + (Bi - n) R_o^{-2n}]}}$$

where n=, 1, 3, 5, 7, . . . ;

$$R = \frac{r}{r_i}; R_o = \frac{r_o}{r_i};$$

$r_i$ is the radius of the inside surface of the wall; $r_o$ is the outside surface of the wall; $q_o$ is the known heat flux; k is the thermal conductivity; Bi is the Biot number, $(r_i h_m / k)$; $h_m$ is the mean heat transfer coefficient of the inside surface; and $\phi = 0$ at the heated part of the plane of symmetry.

7. The method of claim 1, wherein positioning at least some of the temperature measurement devices at different radial positions at the same circumferential location within the wall comprises positioning a plurality of sets of temperature measurement devices at respective axial locations within the wall, each set including a plurality of subsets of temperature measurement devices spaced at respective circumferential locations, each subset including a plurality of temperature measurement devices spaced at different radial locations.

8. The method of claim 1, wherein each of the temperature measurement devices is selected from the group consisting of a thermocouple and a thermistor.

9. The method of claim 1, further comprising directing a heat source with a known heat flux toward approximately one half of the conduit.

10. The method of claim 1, wherein providing a conduit further comprises providing the conduit with an outside perimeter selected from the group consisting of an approximately circular perimeter, an approximately square perimeter and a non-linear perimeter.

11. A system, comprising:
   a conduit having a fluid flowing therethrough;
   a plurality of temperature measurement devices inside a wall of the conduit, the temperature measurement devices operable to detect a plurality of temperatures of the wall;
   at least some of the temperature measurement devices proximate an inside surface of the wall of the conduit;
   at least some of the temperature measurement devices at different radial positions at the same circumferential location within the wall;
   a memory storing a plurality of temperature dependent thermal conductivities of the conduit; and
   a computer operatively coupled to the plurality of temperature measurement devices and the memory, the computer operable to:
   determine a temperature topology of the wall; and
   determine a multi-dimensional thermal characteristic of the inside surface of the wall of the conduit based on extrapolation of the three-dimensional temperature topology and the temperature dependent thermal conductivity.

12. The system of claim 11, wherein the multi-dimensional thermal characteristic comprises a two-dimensional temperature.

13. The system of claim 11, wherein the two-dimensional thermal characteristic comprises a multi-dimensional heat flux.

14. The system of claim 11, wherein the computer is operable to execute an inverse conduction computer code to determine the multi-dimensional thermal characteristic.

15. The method of claim 11, wherein the computer is operable to determine a two-dimensional temperature distribution of the inside surface of the wall of the conduit by solving a dimensionless equation of a generalized form of:

$$T^*(R, \phi) = \frac{T(r, \phi) - T_b}{\left(\frac{q_o r_o}{k}\right)} = \frac{1}{2}\left(\frac{1}{Bi} + \ln R\right) + \sum_{n=1}^{\infty} \frac{2\sin n\left(\phi + \frac{\pi}{2}\right)}{\pi n^2} \frac{R^n}{R_o^n} \frac{(1 - Bi_n R^{-2n})}{(1 + Bi_n R_o^{-2})},$$

where n=1, 3, 5, 7, . . . ;

$$R = \frac{r}{r_i}; R_o = \frac{r_o}{r_i};$$

$r_i$ is the radius of the inside surface of the wall; $r_o$ is the outside surface of the wall; $q_o$ is the known heat flux; k is the thermal conductivity; Bi is the Biot number, $(r_i h_m / k)$; $h_m$ is the mean heat transfer coefficient of the inside surface; $\phi = 0$ at the heated part of the plane of symmetry; and, $$Bi_n = \frac{Bi - n}{Bi + n}.$$

16. The method of claim 11, wherein the computer is operable to determine a two-dimensional heat flux of the inside surface of the wall of the conduit by solving a dimensionless equation of a generalized form of:

$$\frac{q_i(\phi)}{q_o} R_o^{-1} = \frac{1}{2} + \sum_{n=1}^{\infty} \frac{\frac{4\sin n(\phi + \frac{\pi}{2})}{\pi n R_o^n} x}{[(Bi+n)+(Bi-n)R_o^{-2n}]}$$

where n=1, 3, 5, 7, . . . ;

$$R = \frac{r}{r_i}; R_o = \frac{r_o}{r_i};$$

$r_i$ is the radius of the inside surface of the wall; $r_o$ is the outside surface of the wall; $q_o$ is the known heat flux; k is the thermal conductivity; Bi is the Biot number, $(r_i h_m/k)$; $h_m$ is the mean heat transfer coefficient of the inside surface; and $\phi=0$ at the heated part of the plane of symmetry.

17. The system of claim 11, wherein a plurality of sets of temperature measurement devices are at respective axial locations within the wall, each set including a plurality of subsets of temperature measurement devices spaced at respective circumferential locations, each subset including a plurality of temperature measurement devices spaced at different radial locations.

18. The system of claim 11, wherein each of the temperature measurement devices is selected from the group consisting of a thermocouple and a thermistor.

19. The system of claim 11, further comprising a heat source directing a known heat flux toward approximately one half of the conduit.

20. The system of claim 11, wherein the conduit comprises an outside perimeter selected from the group consisting of an approximately circular perimeter, an approximately square perimeter, and a non-linear perimeter.

21. A method, comprising:
providing a conduit having a fluid flowing therethrough;
disposing a plurality of temperature measurement devices inside a wall of the conduit;
positioning at least some of the temperature measurement devices proximate an inside surface of the wall of the conduit;
positioning at least some of the temperature measurement devices at different radial positions at the same circumferential location within the wall;
measuring a plurality of temperatures of the wall with respective ones of the temperature measurement devices to obtain a three-dimensional temperature topology of the wall;
measuring a bulk inlet temperature, a bulk outlet temperature, and a mass flow rate of the fluid;
determining a bulk fluid temperature variation along an axial length of the conduit;
determining the temperature dependent thermal conductivity of the conduit; and
determining the temperature dependent thermal conductivity of the fluid; and
determining the temperature dependent specific enthalpy variation of the fluid; and
determining a multi-dimensional thermal characteristic of the inside surface of the wall of the conduit based on extrapolation of the three-dimensional temperature topology, the temperature dependent thermal conductivity of the conduit, the temperature dependent thermal conductivity of the fluid, the temperature dependent specific enthalpy variation of the fluid, and the bulk fluid temperature variation.

22. The method of claim 21, wherein determining the multi-dimensional thermal characteristic comprises determining a two-dimensional heat transfer coefficient.

23. The method of claim 21, wherein determining the multi-dimensional thermal characteristic further comprises determining a two-dimensional temperature gradient of the fluid.

24. The method of claim 21, wherein determining the multi-dimensional thermal characteristic comprises utilizing an inverse conduction computer code to determine the multi-dimensional thermal characteristic.

25. The method of claim 21, wherein positioning at least some of the temperature measurement devices at different radial positions at the same circumferential location within the wall comprises positioning a plurality of sets of temperature measurement devices at respective axial locations within the wall, each set including a plurality of subsets of temperature measurement devices spaced at respective circumferential locations, each subset including a plurality of temperature measurement devices spaced at different radial locations.

26. The method of claim 21, wherein each of the temperature measurement devices is selected from the group consisting of a thermocouple and a thermistor.

27. The method of claim 21, further comprising directing a heat source with a known heat flux toward approximately one half of the conduit.

28. The method of claim 21, wherein providing a conduit further comprises providing the conduit with an outside perimeter selected from the group consisting of an approximately circular perimeter, an approximately square perimeter and a non-linear perimeter.

29. A system, comprising:
a conduit having a fluid flowing therethrough;
a plurality of temperature measurement devices inside a wall of the conduit, the temperature measurement devices operable to detect a plurality of temperatures of the wall;
a pair of fluid thermocouples operable to detect a bulk inlet temperature and a bulk outlet temperature of the fluid;
a flow meter operable to detect a mass flow rate of the fluid; and
a computer operatively coupled to the plurality of temperature measurement devices, the pair of fluid thermocouples, and flow meter, the computer operable to:
determine a temperature topology of the wall;
determine a bulk fluid temperature variation along an axial length of the conduit; and
determine a multi-dimensional thermal characteristic of an inside surface of the wall of the conduit based on the known heat flux, the temperature topology, the bulk inlet temperature, the bulk outlet temperature, the mass flow rate of the fluid, and the bulk fluid temperature variation.

30. The system of claim 29, wherein the multi-dimensional thermal characteristic comprises a two-dimensional heat transfer coefficient.

31. The system of claim 29, wherein the multi-dimensional thermal characteristic comprises a two-dimensional temperature gradient of the fluid.

32. The system of claim 29, wherein the computer is operable to execute an inverse conduction computer code to determine the multi-dimensional thermal characteristic.

33. The system of claim 29, wherein a plurality of sets of temperature measurement devices are at respective axial locations within the wall, each set including a plurality of subsets of temperature measurement devices spaced at respective circumferential locations, each subset including a plurality of temperature measurement devices spaced at different radial locations.

34. The system of claim 29, wherein each of the temperature measurement devices is selected from the group consisting of a thermocouple and a thermistor.

35. The system of claim 29, further comprising a heat source directing a known heat flux toward approximately one half of the conduit.

36. The system of claim 29, wherein the conduit comprises an outside perimeter selected from the group consisting of an approximately circular perimeter, an approximately square perimeter, and a non-linear perimeter.

* * * * *